United States Patent
Yeung et al.

(10) Patent No.: US 8,449,490 B2
(45) Date of Patent: May 28, 2013

(54) DISC SHUNT DELIVERY WITH STEPPED NEEDLE

(75) Inventors: Jeffrey Yeung, San Jose, CA (US);
Teresa Yeung, San Jose, CA (US);
Andrew Yeung, San Jose, CA (US)

(73) Assignee: Aleeva Medical Inc., San Jose, CA (US)

( * ) Notice: Subject to any disclaimer, the term of this patent is extended or adjusted under 35 U.S.C. 154(b) by 13 days.

(21) Appl. No.: 13/199,906

(22) Filed: Sep. 12, 2011

(65) Prior Publication Data

US 2012/0065570 A1 Mar. 15, 2012

Related U.S. Application Data

(60) Provisional application No. 61/403,188, filed on Sep. 11, 2010.

(51) Int. Cl.
*A61M 27/008* (2006.01)

(52) U.S. Cl.
USPC .......................... 604/8; 604/175; 604/264

(58) Field of Classification Search
None
See application file for complete search history.

(56) References Cited

U.S. PATENT DOCUMENTS

| | | | | |
|---|---|---|---|---|
| 4,409,974 | A * | 10/1983 | Freedland | 606/60 |
| 6,562,033 | B2 * | 5/2003 | Shah et al. | 606/41 |
| 2005/0240201 | A1 * | 10/2005 | Yeung | 606/108 |
| 2007/0142791 | A1 * | 6/2007 | Yeung et al. | 604/264 |
| 2008/0114458 | A1 * | 5/2008 | McKay | 623/17.16 |
| 2009/0312690 | A1 * | 12/2009 | Kim | 604/21 |

FOREIGN PATENT DOCUMENTS
WO  WO2008/013869  *  1/2008

OTHER PUBLICATIONS

Stairmand J.W., Holm S., Urban J.P.G.: Factor influencing oxygen concentration gradients in disc, Spine, vol. 16, 4, 444-449, 1991.
Maroudas A., Stockwell R.A., Nachemson A., Urban J.: Factors involved in the nutrition of the human lumbar intervertebral disc: Cellularity and diffusion of glucose in vitro, J. Anat., 120, 113-130, 1975.
Urban J.P., Smith S., Fairbank J.C.T.: Nutrition of the Intervertebral Disc, Spine, 29 (23), 2700-2709, 2004.
Benneker L.M., Heini P.F., Alini M., Anderson S.E., Ito K.: Vertebral endplate marrow contact channel occlusions & intervertebral disc degeneration, Spine V30, 167-173, 2005.
Holm S., Maroudas A., Urban J.P., Selstam G., Nachemson A.: Nutrition of the intervertebral disc: solute transport and metabolism, Connect Tissue Res., 8(2): 101-119, 1981.
Goel V.K., Monroe B.T., Gilbertson L.G., Brinckman P.: Interlaminar shear stresses and laminae separation in a disc. Spine, 20, 689-98, 1995.
Laible J.P., Pflaster D.S., Krag M.H., Simon B.R., Haugh L.D.: A poroelastic-swelling finite element model with application to the intervertebral disc. Spine, 18, 659-70, 1993.

(Continued)

*Primary Examiner* — Annette Dixon
*Assistant Examiner* — Eric Bryant
(74) *Attorney, Agent, or Firm* — Carol Titus; GSS Law Group

(57) ABSTRACT

A solid stepped needle delivers a disc shunt bridging between muscle and a degenerated disc, drawing blood plasma from muscle into the degenerated disc to alleviate back pain and regenerate the disc. The device further includes pull lines attached to the ends of the disc shunt for withdrawing and repositioning the stepped needle during shunt delivery.

21 Claims, 15 Drawing Sheets

OTHER PUBLICATIONS

Seroussi R.E., Krag M.H., Muller D.L., Pope M.H.: Internal deformations of intact and denucleated human lumbar disc subjected to compression, flexion and extension loads. Journal of Orthopedic Research, 7, 122-131, 1989.

Adams M.A., Hutton W.C.: Mechanics of the intervertebral disc. In the Biology of the Intervertebral Disc, Ghosh P, vol. II, 38-71, CRC Press, Boca Raton, FL, 1988.

Meakin J.R., Hukins D.W.L.: Effect of removing the nucleus pulposus on the deformation of the annulus fibrosus during compression of the intervertebral disc. Journal of Biomechanics, 33, 575-80, 2000.

Yasuma T., Koh S., Okamura T., Yamauchi Y.: Histological changes in aging lumbar intervertebral discs. The Journal of Bone and Joint Surgery, 72-A(2) Feb., 220-9, 1990.

Diamant B., Karlsson J., Nachemson A.: Correlation between lactate levels and pH of patients with lumbar rizopathies, Experientia, 24, 1195-6, 1968.

Nachemson A.: Intradiscal measurements of pH in patients with lumbar rhizopathies. Acta Orthop Scand, 40, 23-43, 1969.

Keshari K.R., Lotz J.C., Link T.M., Hu S., Majumdar S., Kurhanewicz J.: Lactic acid and proteoglycans as metabolic markers for discogenic back pain, Spine, vol. 33(3):312-317, 2008.

Kitano T., Zerwekh J., Usui Y., Edwards M., Flicker P., Mooney V.: Biochemical changes associated with the symptomatic human intervertebral disk, Clinical Orthopaedics and Related Research, 293, 372-377, 1993.

Scott J.E., Bosworth T.R., Cribb A.M., Taylor J.R.: The chemical morphology of age-related changes in human intervertebral disc glycosaminoglycans from cervical, thoracic and lumbar nucleus pulposus and annulus fibrosus. J. Anat., 184, 73-82, 1994.

Dunlop R.B., Adams M.A., Hutton W.C.: Disc space narrowing and the lumbar facet joints, Journal of Bone and Joint Surgery—British Volume, vol. 66-B, Issue 5, 706-710, 1984.

Andersson G.B.J., Schultz A.B.: Effects of fluid on mechanical properties of intervertebral discs, J. Biomechanics, vol. 12, 453-458, 1979.

Gruber H.E., Leslie K., Ingram J., Hoelscher G., Norton H.J., Hanley E.N. Jr.: Colony formation and matrix production by human anulus cells: modulation in three-dimensional culture, Spine, Jul. 1, 29(13), E267-274, 2004.

Johnstone B., Bayliss M.T.: The large proteoglycans of the human intervertebral disc, Changes in their biosynthesis and structure with age, topography, and pathology, Spine, Mar. 15;20(6):674-84, 1995.

Risbud M.V., Gattapalli A., Tsai T.T., Lee J.Y., Danielson K.G., Vaccaro A.G., Albert T.J., Garzit Z., Garzit D., Shapiro I.M.: Evidence for skeletal progenitor cells in the degenerate human intervertebral disc, Spine, Nov. 1;32(23), 2537-2544, 2007.

Ohshima H., Urban J.P.: The effect of lactate and pH on proteoglycan and protein synthesis rates in the intervertebral disc. Spine, Sep. :17(9), 1079-82, 1992.

Wenger D.R., Bobechko W.P., Gilday D.L.: The spectrum of intervertebral disc-space infection in children, J. Bone Joint Surg. Am., 60:100-108, 1978.

Shibayama M., Nagahara M., Kawase G., Fujiwara K., Kawaguchi Y., Mizutani J.: New Needle Biopsy Technique for Lumbar Pyogenic Spondylodiscitis, Spine, Nov. 1, vol. 35—Issue 23, E1347-E1349, 2010.

* cited by examiner

DISC SHUNT DELIVERY WITH STEPPED NEEDLE

CROSS-REFERENCE

This application claims priority of U.S. Provisional Application 61/403,188, entitled Delivery of U-Shaped Disc Shunt With Solid Needle, filed on Sep. 11, 2010 by Jeffrey E. Yeung and Teresa T. Yeung.

FIELD OF INVENTION

A solid stepped needle delivers a disc shunt bridging between muscle and a degenerated disc, drawing blood plasma from muscle into the degenerated disc to alleviate back pain and regenerate the disc. The device further includes pull lines attached to the proximal ends of the disc shunt for withdrawing and repositioning the stepped needle during shunt delivery.

BACKGROUND

Chronic back pain is an epidemic. Nerve impingement is not seen by CT or MRI in about 85% of back pain patients [Deyo R A, Weinstein J N: Low back pain, N Eng J Med, 344(5) February, 363-370, 2001. Boswell M V, et. al.: Interventional Techniques: Evidence-based practice guidelines in the management of chronic spinal pain, Pain Physician, 10:7-111, ISSN 1533-3159, 2007]. In fact, lumbar disc prolapse, protrusion, or extrusion account for less than 5% of all low back problems, but are the most common causes of nerve root pain and surgical interventions (Manchikanti L, Derby R, Benyamin R M, Helm S, Hirsch J A: A systematic review of mechanical lumbar disc decompression with nucleoplasty, Pain Physician; 12:561-572 ISSN 1533-3159, 2009). The cause of chronic back pain in most patients has been puzzling to both physicians and patients.

Studies indicate back pain is correlated with high lactic acid in the disc. Leakage of the acid causes acid burn and persistent back pain. In addition, as the disc degenerates and flattens, the compressive load is shifted from the flattened disc to facet joints, causing strain and pain. Both lactic acid burn and strain of the facet joints are not visible under CT or MRI.

SUMMARY OF INVENTION

A stepped needle has a thin distal end and a protruded step. A disc shunt contains a folded middle portion, first and second end portions. The thin distal end pierces through the folded middle portion, resting on the protruded step to prevent the disc shunt from sliding toward the proximal end of the stepped needle. Both the first and second end portions of the disc shunt drape outside the stepped needle.

Under fluoroscopic guidance, the stepped needle delivers the disc shunt to bridge between a muscle and a degenerated disc. Friction between end portions and disc allows disc shunt deployment by withdrawing the stepped needle from the disc.

Flow of blood plasma through the disc shunt is driven by low osmotic pressure in the muscle to high osmotic pressure in the desiccated disc. Sodium bicarbonate in blood plasma neutralizes the lactic acid; and oxygen reduces anaerobic production of lactic acid to decrease lactic acid burn and persistent pain. Re-supplied nutrients in blood plasma provide building blocks for biosynthesis of new disc matrix for disc regeneration.

| REFERENCE NUMBER | |
|---|---|
| 100 | Disc |
| 101 | Stepped needle |
| 102 | Bevel or tapering |
| 104 | Filament in disc shunt or linked shunt |
| 105 | Endplate |
| 106A | Superior diffusion zone |
| 106B | Inferior diffusion zone |
| 107 | Capillaries |
| 108 | Calcified layer |
| 114 | Delaminated annulus |
| 115 | Epiphysis |
| 118 | Nerve |
| 121 | Fissure |
| 123 | Spinal cord |
| 126 | Disc shunt |
| 126A | U-, V-, folded or middle portion of the disc shunt |
| 126B | First end or portion of the disc shunt |
| 126C | Second end or portion of the disc shunt |
| 127 | Cover, sleeve or wrapping of disc shunt |
| 128 | Nucleus pulposus |
| 129 | Facet joint |
| 131 | Blood plasma containing nutrients, oxygen and buffer chemical |
| 133 | Transverse process |
| 134 | Spinous process |
| 135 | Lamina |
| 142 | Superior articular process |
| 143 | Inferior articular process |
| 159 | Vertebral body |
| 162 | Lactic acid |
| 163 | X-ray contrast agent |
| 165 | Protruded step of the needle |
| 165A | Barb or hook on the step |
| 165B | Indentation of the step |
| 184 | Hole, cavity or vacuole in nucleus |
| 193 | Muscle |
| 194 | Spinal nerve |
| 195 | Posterior longitudinal ligament |
| 276A | Syringe |
| 276B | Injection needle |
| 278 | Pedicle |
| 373 | Linked disc shunt |
| 378 | Annulus |
| 460 | Pull-line |
| 461 | Pull-line retainer or holder |
| 462 | Fold or crease |
| 463 | Knot |
| 503 | Fortified ring or portion of the disc shunt |
| 504 | Kambin's triangle |
| 505 | Skin |
| 506 | Hole in pull line retainer |
| 507 | Neuroforamen |

DETAILED DESCRIPTION OF THE EMBODIMENTS

Figure 1:
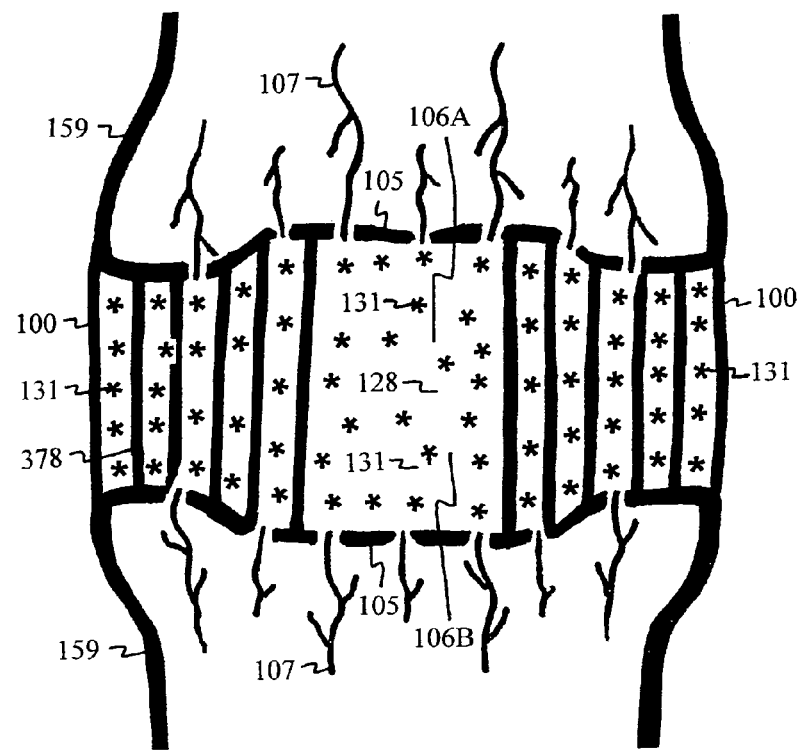
FIG. 1 shows a longitudinal view of a healthy spinal segment with nutrients 131 supplied by capillaries 107 at the endplates 105 to feed the cells within the disc 100.
Figure 2:
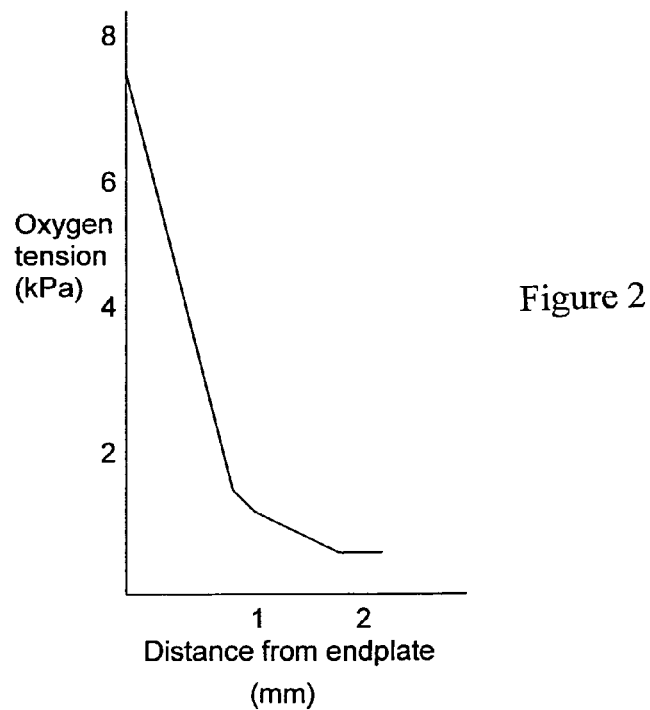
FIG. 2 shows a graph of distance from endplate into a disc versus oxygen concentration.

Intervertebral discs are avascular (no blood vessels). Nutrients, oxygen and pH buffer 131 essential for disc cells are diffused from capillaries 107 at the superior and inferior endplates 105 into the disc 100. A longitudinal view of a vertebral segment is shown in FIG. 1. However, depth of diffusion is shallow into thick human discs 100. The calculated depth of oxygen diffusion from the endplates 105 is summarized in FIG. 2 (Stairmand J W, Holm S, Urban J P G: Factor influencing oxygen concentration gradients in disc, Spine, Vol. 16, 4, 444-449, 1991).

Similarly, calculated depths of glucose diffusion are less than 3 mm from superior and inferior endplates (Maroudas A, Stockwell R A, Nachemson A, Urban J: Factors involved in the nutrition of the human lumbar intervertebral disc: Cellularity and diffusion of glucose in vitro, J. Anat., 120, 113-130, 1975). Nearly all animals have thin discs, so depths of diffusion of nutrients and oxygen seem to be sufficient. Lumbar discs of a large sheep weighing 91 kg (200 pounds) are less than 3 mm thick. However, human lumbar discs are about 7-12 mm thick. Mid layers of our thick discs are highly vulnerable to severe oxygen and nutritional deficiencies.

Figure 3:
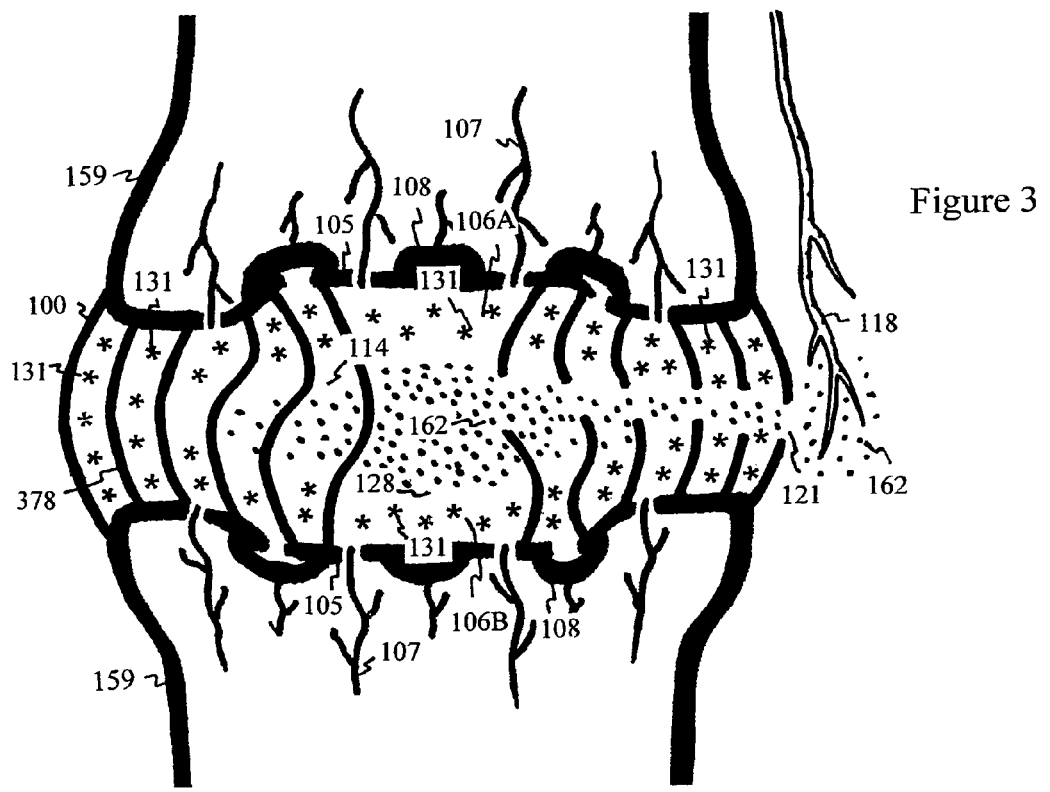
FIG. 3 shows calcified layers 108 accumulated at the endplates 105, blocking diffusion of nutrients/oxygen 131 from capillaries 107, forming and leaking lactic acid 162 to irritate a nerve 118.

As we age, calcified layers 108 form and accumulate at the endplates 105, block capillaries 107 and further reduce the depth of diffusion of nutrients/oxygen/pH buffer 131 into the disc 100, as shown in FIG. 3. Cell death, matrix degradation and lactic acid 162 accumulation due to starvation and anaerobic conditions are common in the mid layer of the avascular discs 100. Degradation of glycosaminoglycans may provide sugars to fuel the production of lactic acid 162. [Urban J P, Smith S, Fairbank J C T: Nutrition of the Intervertebral Disc, Spine, 29 (23), 2700-2709, 2004. Benneker L M, Heini P F, Alini M, Anderson S E, Ito K: Vertebral endplate marrow contact channel occlusions & intervertebral disc degeneration, Spine V30, 167-173, 2005. Holm S, Maroudas A, Urban J P, Selstam G, Nachemson A: Nutrition of the intervertebral disc: solute transport and metabolism, Connect Tissue Res., 8(2): 101-119, 1981].

When glycosaminoglycans diminish, water content and swelling pressure of the nucleus pulposus 128 decrease. The nucleus 128 with reduced swelling pressure can no longer distribute forces evenly against the circumference of the inner annulus 378 to keep the annulus bulging outward. As a result, the inner annulus 378 sags inward while the outer annulus 378 bulges outward, creating annular delamination 114 and weakened annular layers 378, possibly initiating fissure 121 formation depicted in FIGS. 3 and 4. [Goel V K, Monroe B T, Gilbertson L G, Brinckman P: Interlaminar shear stresses and laminae separation in a disc. Spine, 20, 689-98, 1995. Laible J P, Pflaster D S, Krag M H, Simon B R, Haugh L D: A poroelastic-swelling finite element model with application to the intervertebral disc. Spine, 18, 659-70, 1993. Seroussi R E, Krag M H, Muller D L, Pope M H: Internal deformations of intact and denucleated human lumbar disc subjected to compression, flexion and extension loads. Journal of Orthopedic Research, 7, 122-131, 1989. Adams Mass., Hutton W C: Mechanics of the intervertebral disc. In The Biology of the Intervertebral Disc, Ghosh P, Vol. II, 38-71, CRC Press, Boca Raton, Fl., 1988. Meakin J R, Hukins D W L: Effect of removing the nucleus pulposus on the deformation of the annulus fibrosus during compression of the intervertebral disc. Journal of Biomechanics, 33, 575-80, 2000. Yasuma T, Koh S, Okamura T, Yamauchi Y: Histological changes in aging lumbar intervertebral discs. The Journal of Bone and Joint Surgery, 72-A(2) February, 220-9, 1990].

High lactic acid content in discs correlates with back pain. In fact, dense fibrous scars and adhesions, presumably from lactic acid 162 burn, can be found around nerve roots 194 during spinal surgery [Diamant B, Karlsson J, Nachemson A: Correlation between lactate levels and pH of patients with lumbar rizopathies, Experientia, 24, 1195-6, 1968. Nachemson A: Intradiscal measurements of pH in patients with lumbar rhizopathies. Acta Orthop Scand, 40, 23-43, 1969. Keshari K R, Lotz J C, Link T M, Hu S, Majumdar S, Kurhanewicz J: Lactic acid and proteoglycans as metabolic markers for discogenic back pain, Spine, Vol. 33(3):312-317, 2008].

Figure 4:
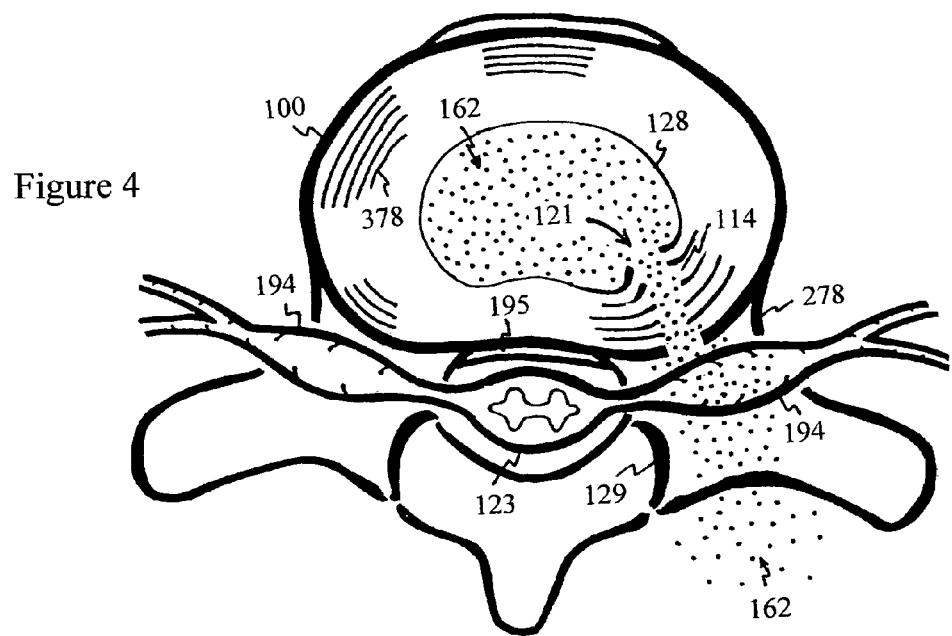
FIG. 4 shows leakage of lactic acid 162, burning or irritating the spinal nerve 194.

Under anaerobic conditions within the disc nucleus 128, lactic acid 162 is produced and leaked from the nucleus 128 through fissures 121 to burn surrounding nerves 118 causing persistent back pain, as depicted in FIGS. 3 and 4. Some patients experience leg pain without visible spinal nerve impingement under MRI or CT. Lactic acid 162 can leak from the nucleus 128 through fissures 121 to spinal nerves 194, causing leg pain as depicted in FIG. 4. Leg pain without visible impingement is commonly called chemical radiculitis.

Figure 5:
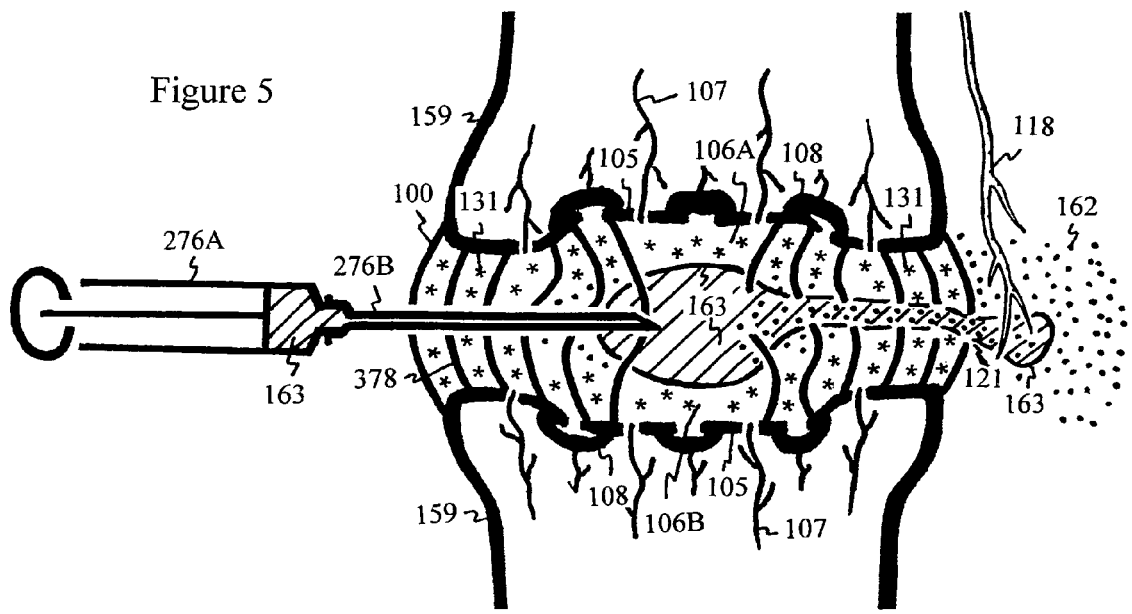
FIG. 5 depicts diagnostic discography by flushing lactic acid 162 to sensory nerve 118 with contrast agent 163 to confirm pain.

Discography is a common diagnostic technique for identifying or confirming a painful disc 100 before surgical intervention. Intradiscal injection of an X-ray contrast 163 flushes the lactic acid 162 from the nucleus 128 through fissures 121 to adjacent nerves 118, causing instant and excruciating pain, as shown in FIG. 5. For normal or non-painful discs, discography with mild injection pressure is nearly painless.

Composition of Intervertebral Discs (approximation)

| | Normal Discs | Painful Discs | % Change from Normal Discs |
|---|---|---|---|
| Glycosaminoglycans | 27.4 ± 2.4% | 14.1 ± 1.1% | −48.5% |
| Collagen | 22.6 ± 1.9% | 34.8 ± 1.4% | +54% |
| Water content | 81.1 ± 0.9% | 74.5 ± 1% | −8.1% |
| Acidity | pH 7.14 [$H^+$]: $7.20 \times 10^{-8}$ | pH 6.65-5.70 [$H^+$]: $2.23 \times 10^{-7}$ to $2.00 \times 10^{-6}$ | [$H^+$]: +208% to +2,661% |

(Reference: Kitano T, Zerwekh J, Usui Y, Edwards M, Flicker P, Mooney V: Biochemical changes associated with the symptomatic human intervertebral disk, Clinical Orthopaedics and Related Research, 293, 372-377, 1993. Scott J E, Bosworth T R, Cribb A M, Taylor J R: The chemical morphology of age-related changes in human intervertebral disc glycosaminoglycans from cervical, thoracic and lumbar nucleus pulposus and annulus fibrosus. J. Anat., 184, 73-82, 1994. Diamant B, Karlsson J, Nachemson A: Correlation between lactate levels and pH of patients with lumbar rizopathies, Experientia, 24, 1195-1196, 1968. Nachemson A: Intradiscal measurements of pH in patients with lumbar rhizopathies, Acta Orthop Scand, 40, 23-43, 1969.)

Figure 6:
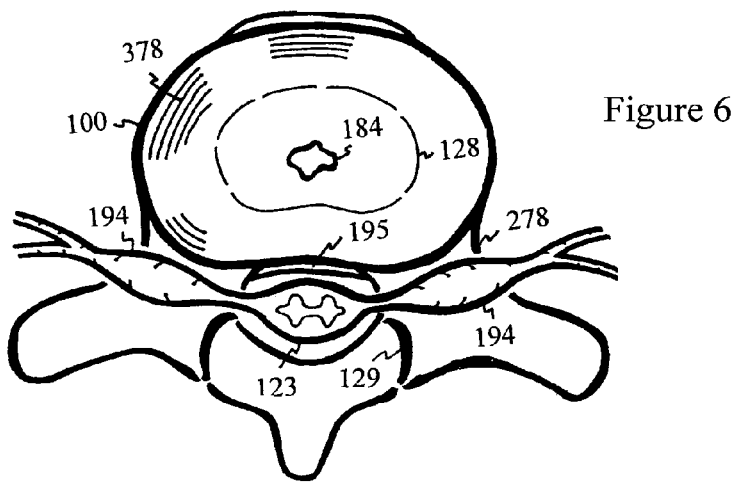
FIG. 6 shows a hole or vacuole 184 in the disc 100.
Figure 7:
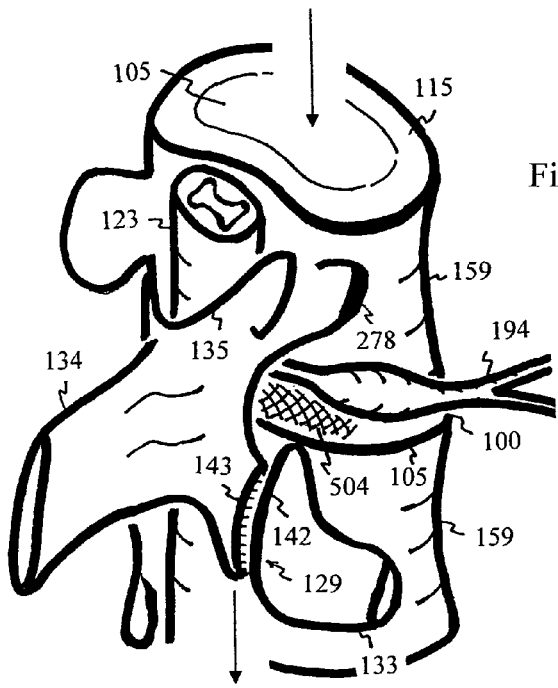
FIG. 7 shows load transfer from the flattened and degenerated disc 100 to facet joint 129, straining ligament between superior 142 and inferior 143 articular processes.

Disc cells can survive without oxygen, but will die without glucose. The central area in the mid layer of the disc 100 is most vulnerable to glucose deficiency and cell death. Holes or vacuoles 184 can be found during dissections of cadaveric discs 100, as shown in FIG. 6. Nuclei pulposi 128 of degenerated discs 100 are usually desiccated, with reduced swelling pressure and decreased capability to sustain compressive loads. The compressive load is thus transferred to the facet joints 129, pressing the inferior articular process 143 against the superior articular process 142 of the facet joint 129, causing strain, wear and/or pain as shown in FIG. 7 (Dunlop R B, Adams M A, Hutton W C: Disc space narrowing and the lumbar facet joints, Journal of Bone and Joint Surgery—British Volume, Vol 66-B, Issue 5, 706-710, 1984).

Figure 8:
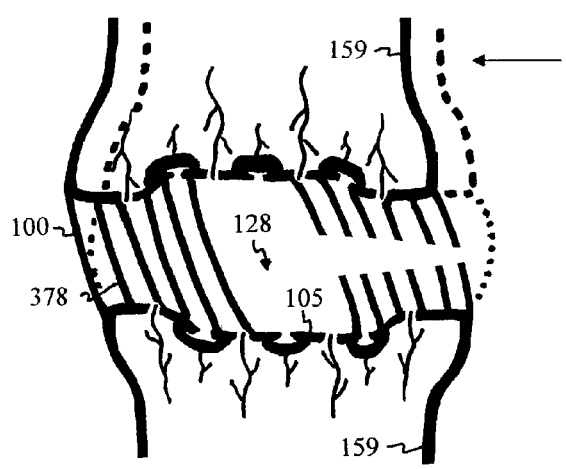
FIG. 8 depicts swaying of a vertebral body 159 above a flattened disc 100 with low-swelling pressure.
Figure 9:
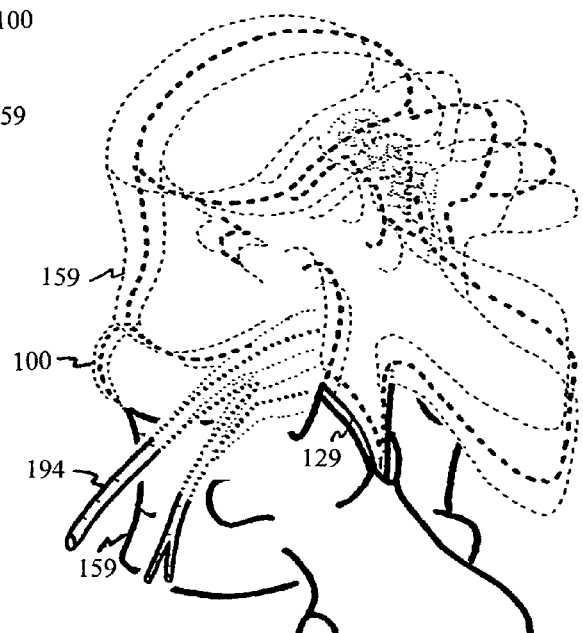
FIG. 9 depicts spinal instability from the low-pressure disc 100, straining and wearing down the facet joints 129.

A disc 100 with reduced swelling pressure is similar to a flat tire with flexible or flabby side walls. The vertebral body 159 above the soft or flabby disc 100 easily shifts or sways, as shown in FIG. 8. This is commonly called segmental or spinal instability. As shown in FIG. 9, the frequent or excessive movement of the vertebral body 159 strains the facet joints 129. Patients with spinal instability often use their muscles to guard or support their spines to ease facet pain. As a result, muscle tension and aches arise, but are successfully treated with muscle relaxants. Spinal motions, including compression, torsion, extension, flexion and lateral bending, were measured before and after saline injection into cadaveric discs. Intradiscal saline injections reduced all spinal motions in the cadaveric study (Andersson G B J, Schultz A B: Effects of fluid on mechanical properties of intervertebral discs, J. Biomechanics, Vol. 12, 453-458, 1979).

Figure 10:
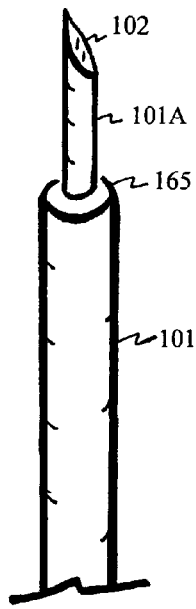
FIG. 10 shows a stepped needle 101 containing a beveled end 102 and a protruded step 165.
Figure 10A:
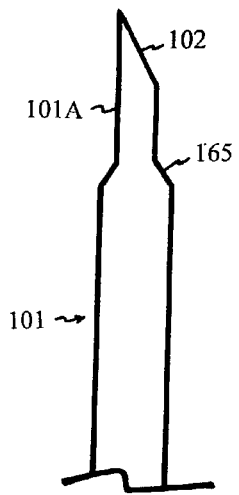
FIG. 10A shows a longitudinal view of the protruded step 165 with a slope to facilitate disc puncturing.
Figure 11:
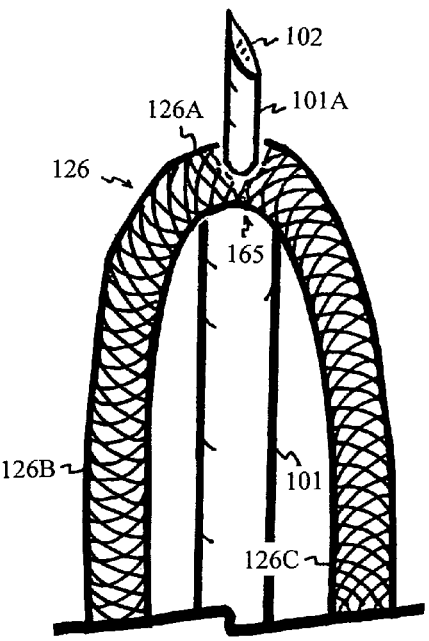
FIG. 11 shows a disc shunt 126 pierced through by distal end 101A of the stepped needle 101, resting on the protruded step 165.

A stepped needle 101 contains a beveled or sharp tip 102 at the distal end, a protruded step 165 proximal to the sharp tip 102, as shown in FIG. 10. The stepped needle 101 is a solid needle, without a longitudinal lumen. A thin portion 101A is located between the sharp tip 102 and the protruded step 165. Orientation of the protruded step 165 can be angled, other than 90 degree protruded from the shaft of the needle 101, as shown in FIG. 10A. The sharp tip 102 and the thin portion 101A of the stepped needle 101 is used to puncture or thread through a disc shunt 126. The protruded step 165 prevents the disc shunt 126 from sliding or moving proximally along the stepped needle 101, as shown in FIG. 11.

Figure 15:
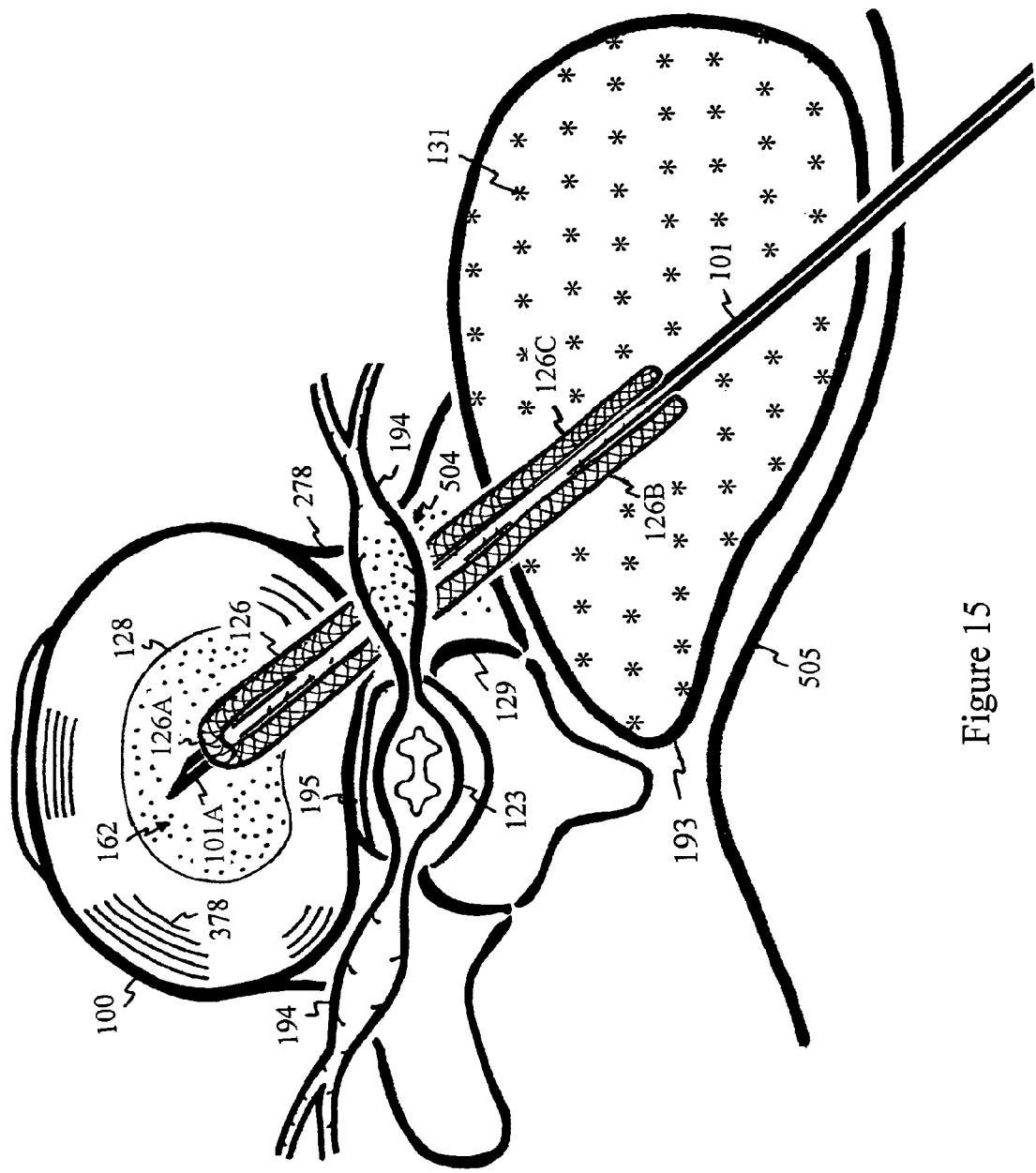
FIG. 15 shows the stepped needle carrying the disc shunt 126 puncturing through skin 505 to bridge between muscle 193 and the degenerated disc 100.

The disc shunt 126 is made of a linear strand, containing a middle portion 126A, a first portion 126B and a second portion 126C. The disc shunt 126 is folded at the middle portion 126A into a U-, V-, or folded portion 126A. The thin portion 101A of the stepped needle 101 pierces, threads or pins through the folded or middle portion 126A. The non-spiraled middle portion 126A surrounds or encircles the thin portion 101A distal to the protruded step 165 of the stepped needle 101. Both the first 126B and second 126C portions of the disc shunt 126 drape over the outside wall of the stepped needle 101, as shown in FIG. 11. The middle portion 126A becomes the distal end, and the first 126B and second 126C portions become the proximal end of the disc shunt 126, as shown in FIGS. 11 and 15. The first portion 126B can be called the first end 126B; the second portion 126C can be called the second end 126C.

The U-, V-, folded or middle portion 126A can be thinner than the first 126B and second 126C portions of the disc shunt 126, to minimize the size of the folded portion 126A and the protruded step 165 for disc 100 puncturing.

The middle portion 126A can also contain a fortified ring or segment 503, sized and configured to fit around the thin portion 101A and sit on the protruded step 165 of the stepped needle 101.

Figure 13:
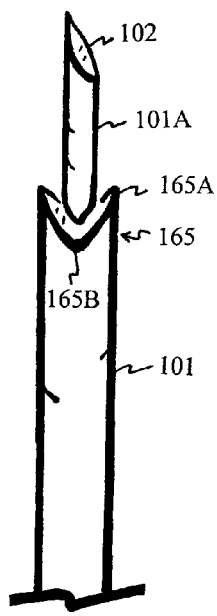
FIG. 13 shows the protruded step 165 containing at least one barb 165A and at least one indentation 165B. The barb 165A can pierce, hook, hold or retain the disc shunt 126.
Figure 12:
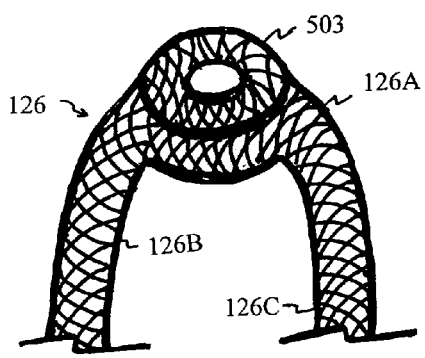
FIG. 12 shows a fortified ring 503 on the disc shunt 126, sized and configured to sit or rest on the protruded step 165.
Figure 14:
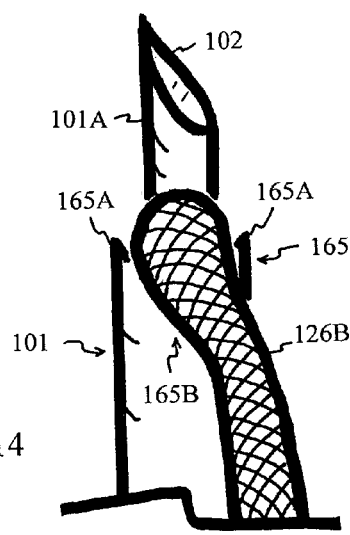
FIG. 14 shows formation of a saddle of the disc shunt 126 supported by the barbs 165A and indentations 165B.

The protruded step 165 can contain at least one barb 165A and at least one indentation 165B, as shown in FIG. 13. The barb 165A can be used to pierce, hook or anchor the middle portion 126A of the disc shunt 126. The barbs 165A and indentations 165B can also form a saddle to position the middle portion 126A of the disc shunt 126, as shown in FIG. 14.

Similar to discography, the stepped needle 101 carrying the disc shunt 126 is guided by a fluoroscope, puncturing through skin 505 and muscle 193 into a safe entry called Kambin's Triangle 504, outlined by the facet joint 129, spinal nerve 194 and endplate 105 beneath the degenerated disc 100, as depicted in FIG. 15. The stepped needle 101 spearheads or punctures tissue to pull the U- or middle portion 126A, the first end 126B and the second end 126C to squeeze or press-fit into the muscle 193 and disc 100, as shown in FIG. 15.

Figure 16:
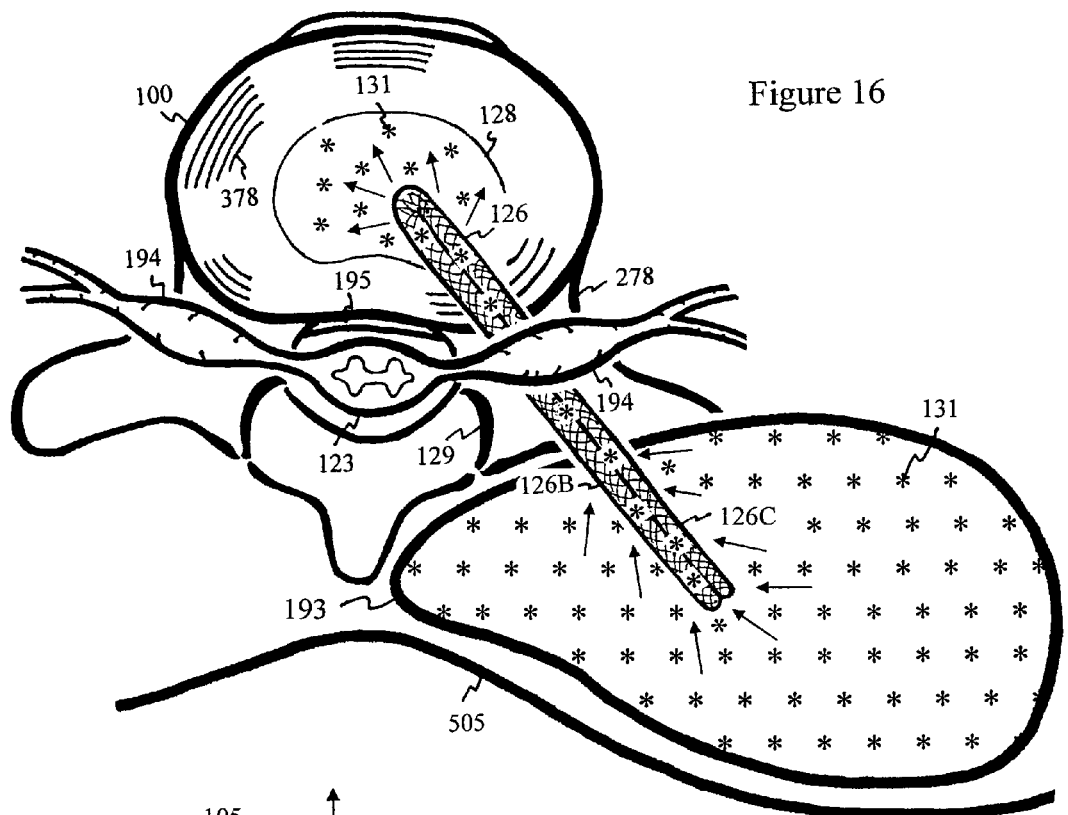
FIG. 16 shows deployment of the disc shunt 126 by withdrawing the stepped needle, to draw blood plasma 131 from well hydrated muscle 193 into the desiccated disc 100.

The stepped needle 101 is visible under fluoroscope. After confirming proper location of the stepped needle 101 by anterior/posterior and lateral fluoroscopic views, the stepped needle 101 is withdrawn, deploying the disc shunt 126 to bridge between the muscle 193 and degenerated disc 100, as shown in FIG. 16. Deployment of the disc shunt 126 is facilitated by friction between the disc shunt 126 and tissues. Friction between shunt portions 126B, 126C and tissue is significantly higher than friction between the shaft of stepped needle 101 and shunt portions 126B, 126C. Therefore, withdrawal of the stepped needle 101 deploys the disc shunt 126 to bridge, joint or connect the moist muscle 193 to the desiccated disc 100, in FIG. 16.

Fluid flows from low to high osmolarity. Osmolarity of human blood plasma 131 in muscle 193 is 265-299 mOsm/liter, and osmolarity in human discs 100 is 300-400 mOsm/liter. Disc shunt 126 is a wick, drawing plasma 131 from muscle 193 with low osmotic pressure to the degenerated disc 100 with high osmotic pressure, as shown in FIG. 16.

Blood plasma 131 in muscle 193 is rich in water, nutrient, oxygen and pH buffer 131. On the other hand, due to the avascular nature and calcified layers 108 on the endplates 105, nutrient, oxygen and pH buffer 131 are extremely low within the intervertebral discs 100, as shown in FIG. 3. Degenerated discs 100 are desiccated, visible as black disc 100 under T2 MRI. In addition, degenerated discs 100 usually contain a high concentration of lactic acid 162 [Diamant B, Karlsson J, Nachemson A: Correlation between lactate levels and pH of patients with lumbar rizopathies, Experientia, 24, 1195-6, 1968. Nachemson A: Intradiscal measurements of pH in patients with lumbar rhizopathies. Acta Orthop Scand, 40, 23-43, 1969. Keshari K R, Lotz J C, Link T M, Hu S, Majumdar S, Kurhanewicz J: Lactic acid and proteoglycans as metabolic markers for discogenic back pain, Spine, Vol. 33(3):312-317, 2008].

Normal blood pH is tightly regulated between 7.35 and 7.45, mainly by the pH buffering sodium bicarbonate 131 dissolved in blood plasma 131. Sodium bicarbonate 131 in blood plasma 131 permeates, transports or diffuses through disc shunt 126 to neutralize lactic acid 162 in the degenerated disc 100 to relieve acid burn and persistent back pain. Oxygen dissolved in plasma 131 decreases the anaerobic production of lactic acid 162 within the disc 100 to further reduce acid burn and back pain.

Figure 17:
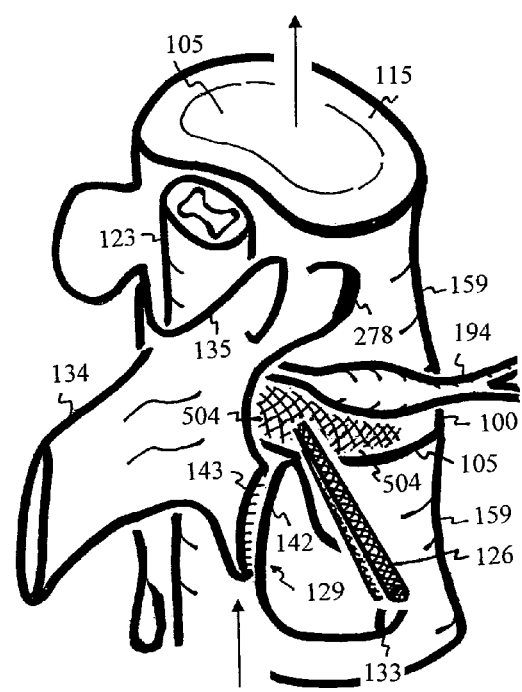
FIG. 17 shows the rehydrated or re-inflated disc 100 by blood plasma transported through the disc shunt 126 to shift load from facet joints 129 to the re-inflated disc 100.

Water in blood plasma 131 through disc shunt 126 hydrates the desiccated nucleus 128 to sustain compressive load, as shown in FIG. 16. The continual supply of nutrients in plasma 131 becomes building blocks for new disc matrix, adding cushion or bulk within the shunted disc 100. As a result, disc height is increased by nucleus 128 hydration and newly developed disc matrix to shift the compressive load from painful facet joints 129 to shunted disc 100, as shown in FIG. 17. Hence, facet 129 pain is relieved from compressive loading and segmental instability.

Figure 18:
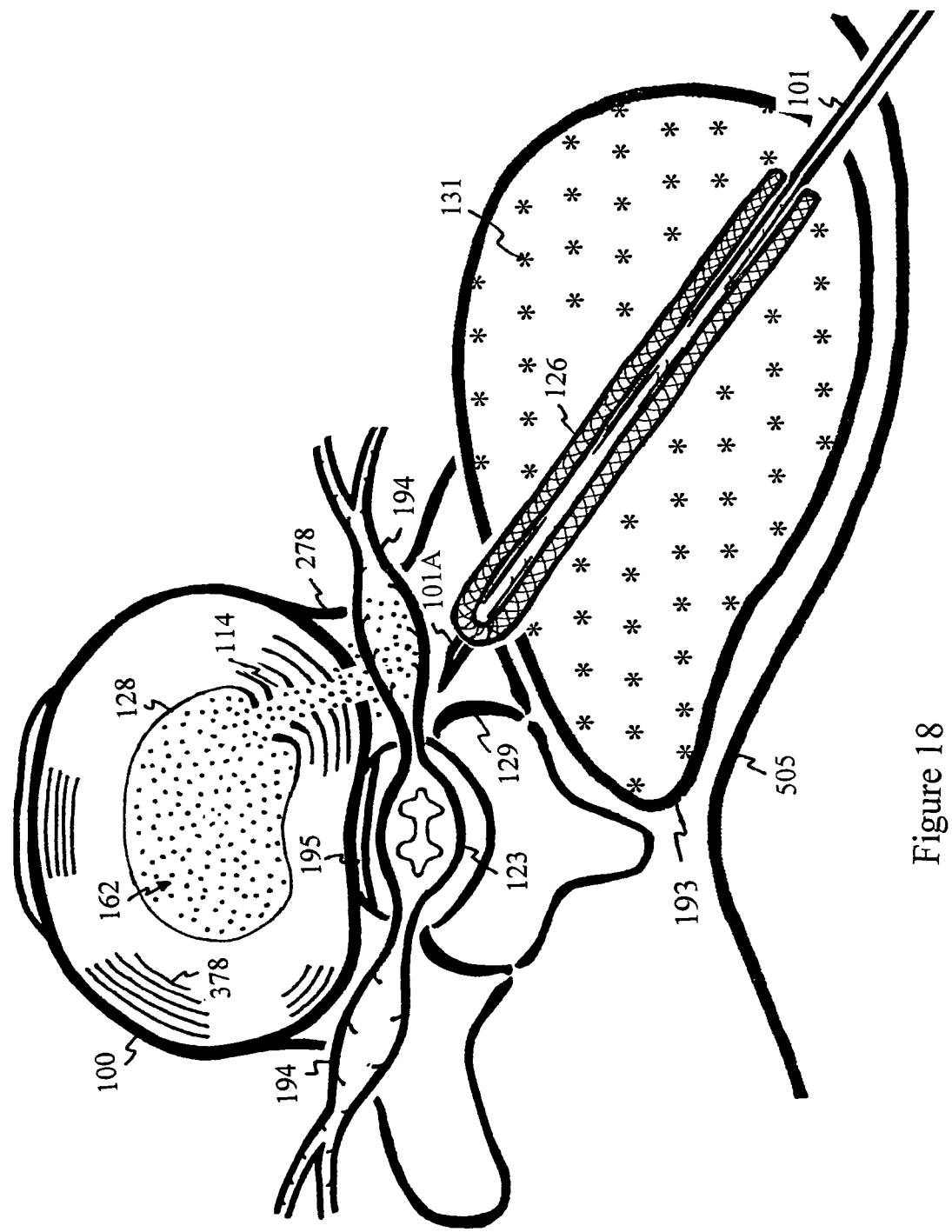
FIG. 18 shows a misdirected stepped needle 101 toward the spinal cord 123, visible under fluoroscope.
Figure 19:
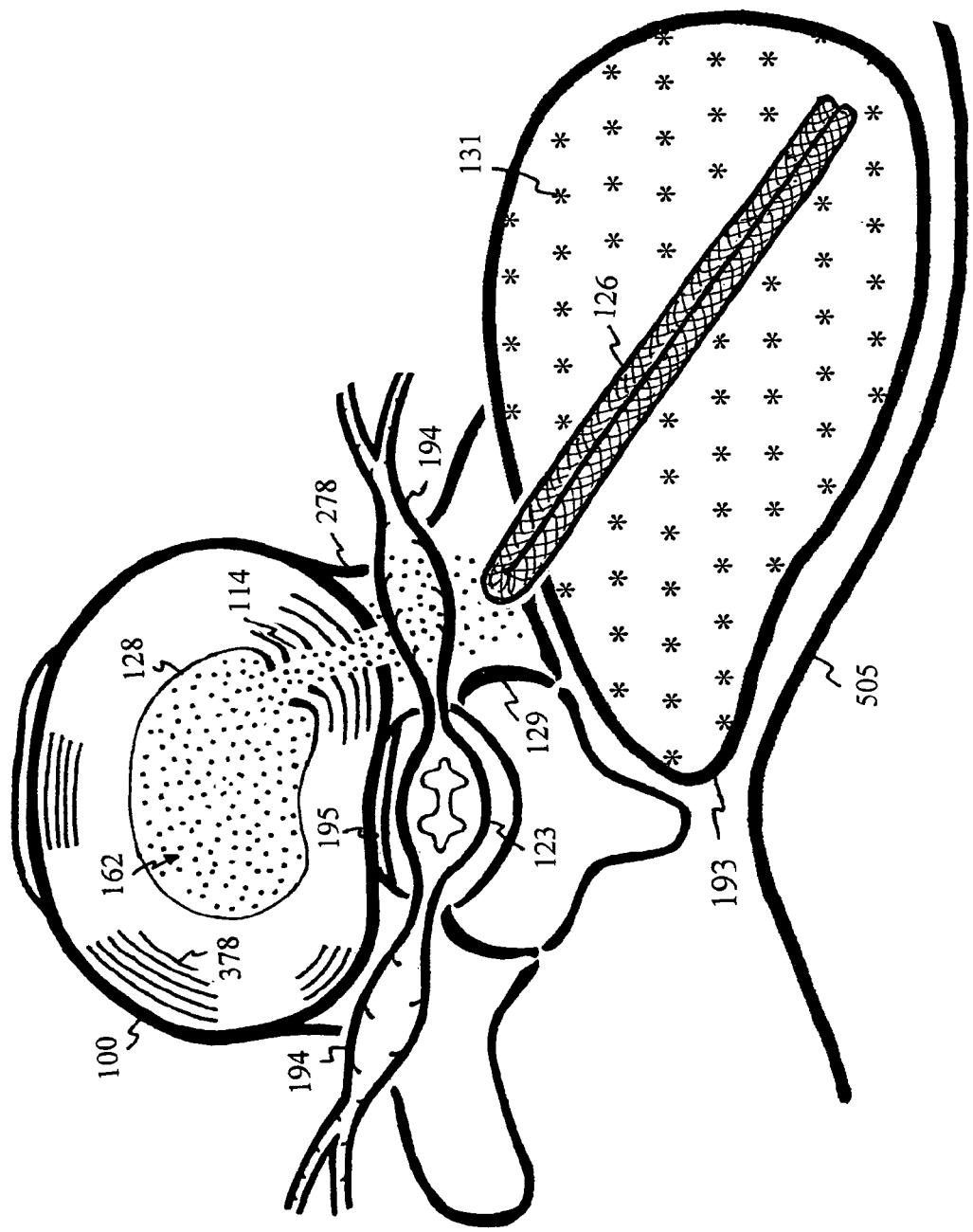
FIG. 19 shows premature deployment of the disc shunt 126 by withdrawing the stepped needle during redirection toward the disc 100.

Aiming a spinal needle 276B toward Kambin's Triangle 504 for discography often requires redirecting by partial withdrawal and re-insertion of the needle 276B. Similarly, the stepped needle 101 may also require redirecting. Location of the stepped needle 101 carrying the disc shunt 126 is visible under anterior/posterior and lateral views of fluoroscope. FIG. 18 shows the stepped needle 101 advancing toward the spinal cord 123, needing partial withdrawal of the stepped needle 101 for redirecting. However, partial withdrawal of the stepped needle 101 will prematurely deploy the disc shunt 126 as shown in FIG. 19.

Figure 20:
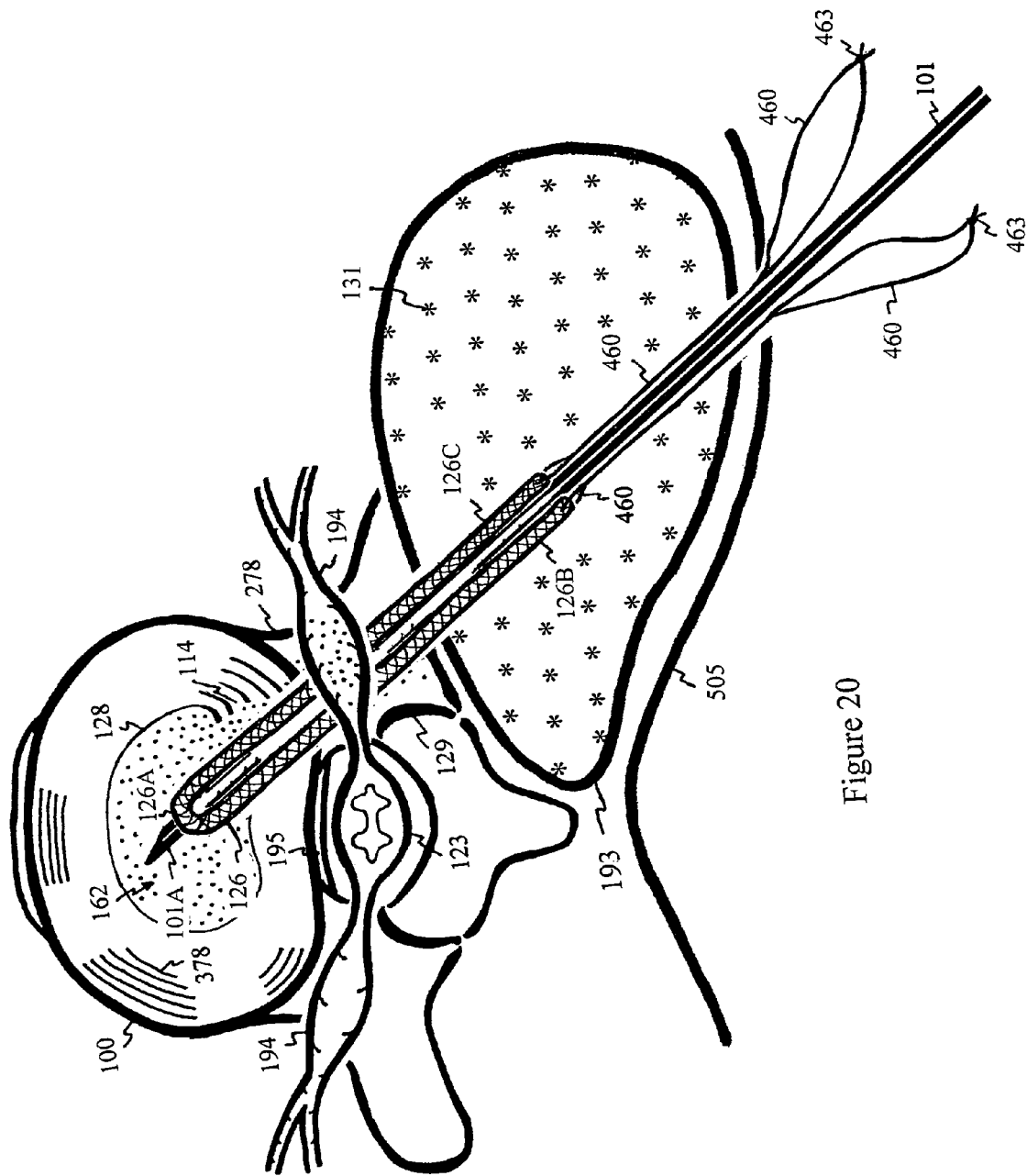
FIG. 20 shows a pair of pull lines 460 extending above the skin 505 for applying tension during partial withdrawal and redirection of the stepped needle 101.
Figure 21:
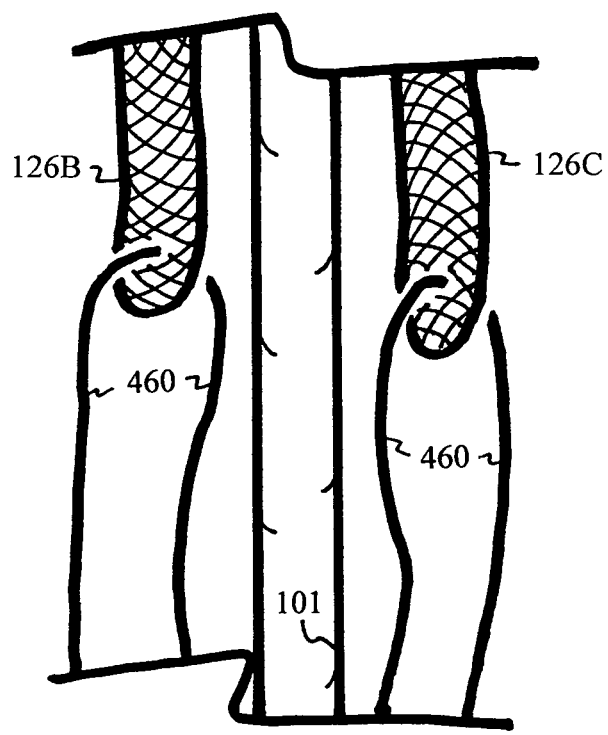
FIG. 21 shows the pair of pull lines 460 which connect or engage proximal ends 126B, 126C of the disc shunt 126.
Figure 22:
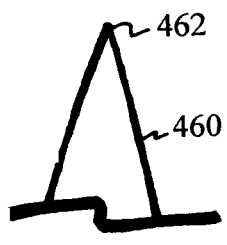
FIG. 22 depicts tension applied on the pull line 460 forming a fold or crease 462 at the junction between the pull line 460 and disc shunt 126.
Figure 23:
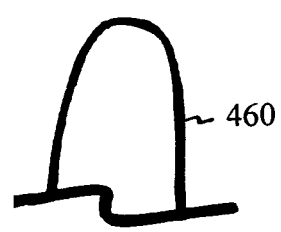
FIG. 23 depicts released tension of the crease-resistant pull line 460.

FIG. 20 shows pull lines 460 attached to the first end 126B and the second end 126C of the disc shunt 126. The pull line 460 can be a loop, joined by a knot 463 outside the skin 505. If the needle 101 is misguided under fluoroscopic view, tension is applied to the pull lines 460 during partial withdrawal of the needle 101. Tension on the pull lines 460 keeps the distal portion 126A of the shunt 126 on the protruded step 165 of the withdrawing stepped needle 101 for redirection toward the Kambin's Triangle 504. The pull lines 460 can thread through or attach to the first end 126B and second end 126C of the disc shunt 126, as shown in FIG. 21. The pull line 460 can be made with crease or fold-resistant material. Under tension, crease or fold 462 appears on the pull line 460 at the connection or junction between the pull line 460 and disc shunt 126, as depicted in FIG. 22. When the tension is released, the fold or crease 462 disappears from the crease-resistant pull line 460, as shown in FIG. 23. After confirming proper location of the stepped needle 101 under fluoroscope, the loops of pull lines 460 are cut and retrieved by pulling the pull lines 460 from the first 126B and second 126C ends of the disc shunt 126 beneath the skin 505. The stepped needle 101 is then withdrawn to deploy the disc shunt 126, bridging, joining, connecting, communicating or transporting between the muscle 193 and the disc 100.

The kink resistant pull line 460 can be a mono-filament made with nylon, polypropylene, biodegradable material or other materials. The kink resistant pull line 460 can be a suture.

Figure 24:
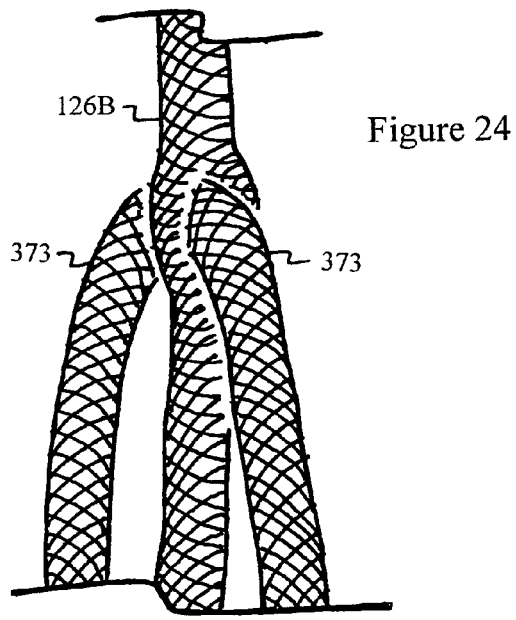
FIG. 24 shows a linked shunt 373 connecting to or engaging the disc shunt 126.
Figure 25:
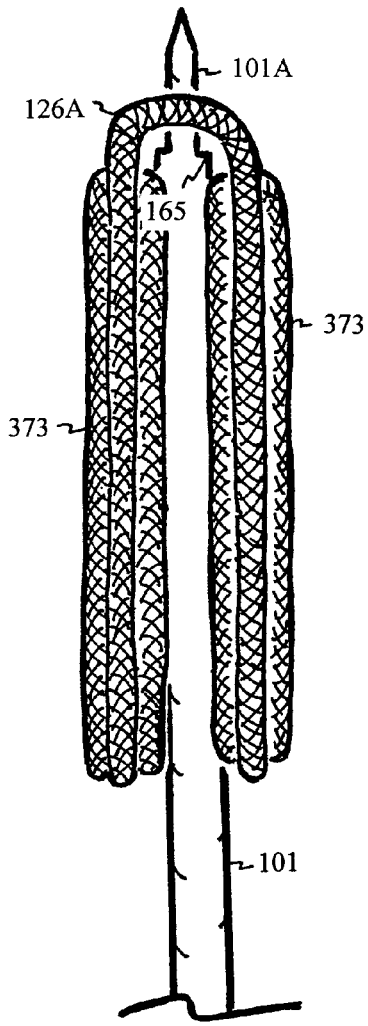
FIG. 25 shows a longitudinal view of the stepped needle 101 engaging the disc shunt 126 connecting to the linked shunts 373 for delivery into degenerated disc.
Figure 26:
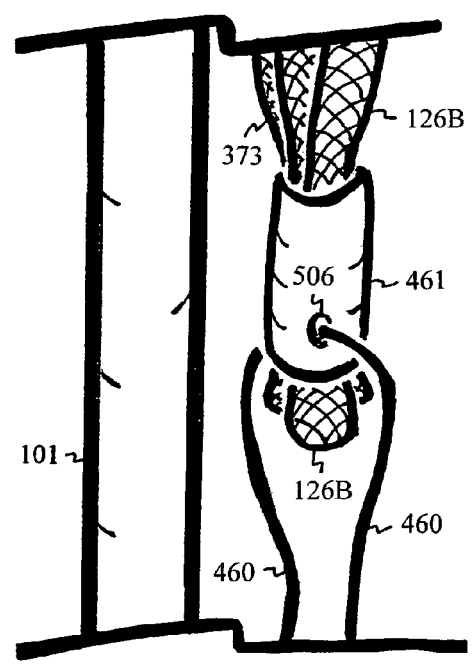
FIG. 26 shows a retainer or holder 461 of the disc shunt 126 and linked shunt 373, connecting to a pull line 460.

The amount of fluid transported into the shunted disc 100 is related to the size of the disc shunt 126. A linked shunt 373 can be attached to or threaded through the disc shunt 126, as shown in FIG. 24, to increase plasma 131 transport. The stepped needle 101 is loaded with the disc shunt 126, and the linked shunts are connected to the disc shunt 126, as shown in FIG. 25. For ease of disc 100 puncturing, the linked shunts 373 are preferred to be positioned for sequential entry, one after another into the degenerated disc 100. The pull line 460 can also attach to the linked shunt 373 and the first 126B or second 126C end through a pull-line holder 461, as shown in FIG. 26.

Figure 27:
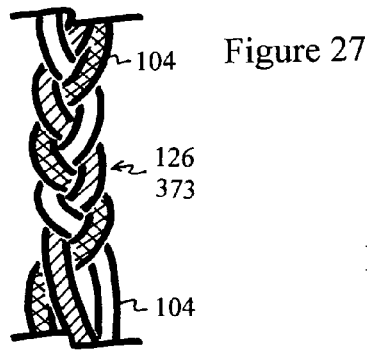
FIG. 27 shows braided filaments 104 forming the disc shunt 126 or linked shunt 373.
Figure 28:
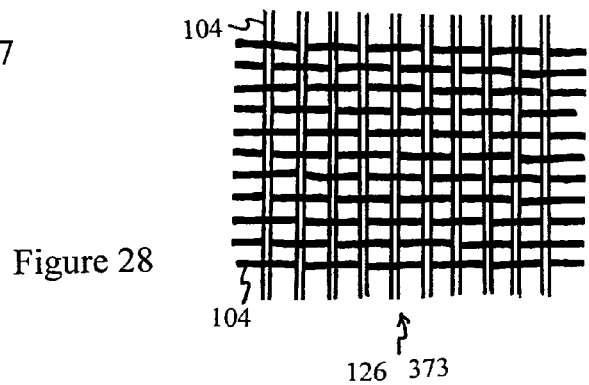
FIG. 28 shows woven filaments 104 forming the disc shunt 126 or linked shunt 373.
Figure 29:
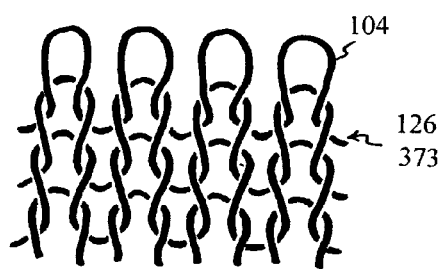
FIG. 29 shows knitted filaments 104 forming the disc shunt 126 or linked shunt 373.

Flexible disc shunt 126 or linked shunt 373 can be made or formed by fabric making techniques, such as braiding or twisting filaments 104 as shown in FIG. 27. For twisting, minimum number of filaments 104 is two. For braiding, minimum number of filaments 104 is three, as shown in FIG. 27. Braiding is intertwining three or more filaments 104 for excellent flexibility, strength and porosity. The flexible disc shunt 126 or linked shunt 373 can also be woven, as shown in FIG. 28. Weaving is interlacing the filaments 104 over and under each other, generally oriented at 90 degree angles. Half of the filaments 104 from weaving can be oriented lengthwise along the linear shunt 126 or linked shunt 373 to expedite fluid flow from the muscle 193 into the degenerated disc 100. The flexible disc shunt 126 or linked shunt 373 can be knitted, as shown in FIG. 29. Knitting is a construction made by interlocking loops of one or more filaments 104. Knitted shunt strands 104 may have the greatest elasticity, capable of stretching and elongating during the press-fitted delivery into the disc 100. After the disc shunt 126 or linked shunt 373 is deployed within the disc 100, the diameter of the disc shunt 126 or linked shunt 373 in the disc 100 expands, further sealing the needle 101 tract to prevent the loss of hydrostatic pressure within the disc 100. In addition, the knitted shunt 126 or linked shunt 373 has the highest porosity to enhance fluid absorbency, creating a reservoir of nutrients/oxygen/pH buffer 131 for dispersing into various parts of the avascular disc 100, as shown in FIG. 16. Furthermore, knitted filaments 104 in the disc shunt 126 or linked shunt 373 provide an elastic cushion within the disc 100. The knitted disc shunt 126 or linked shunt 373 may be an excellent matrix or scaffolding for cell attachment and proliferation. The disc shunt 126 or linked shunt 373 can be made with non-woven filaments 104. The term non-woven is used in fabric industry to include all other techniques, such as carded/needle-punched, spun bonded, melt blown or other. Non-woven disc shunt 126 or linked shunt 373 provides large surface area as scaffolding for cell growth and proliferation. Combinations of fabric making techniques can be used to form the disc shunt 126 or linked shunt 373. The disc shunt 126 and the linked shunt 373 can be made with different material or different fabric making techniques. For example, the disc shunt 126 can be made primarily for fluid transport, while the linked shunt 373 can be made primarily for cell attachment and proliferation. The disc shunt 126 and the linked shunt 373 can be coated with different drugs to alleviate back pain and/or promote disc 100 regeneration.

Material and/or orientation of the filaments 104 of the disc shunt 126 or linked shunt 373 can affect (1) flow rate, (2) tensile strength, (3) annular sealing, (4) porosity, (5) fluid absorbency, (6) strength for filament separation, (7) elasticity, (8) selectivity of solute transport, (9) scaffold attachment of cells, (10) flexibility, (11) durability, (12) sterilization technique, (13) fibrotic formation, and/or (14) biocompatibility.

Figure 30:
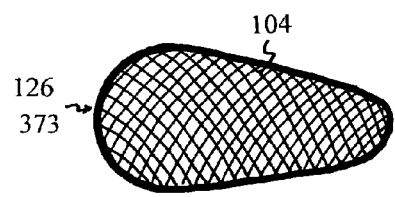
FIG. 30 depicts a slant cut showing the slanted orientations of filaments 104 relative to the length-wise disc shunt 126 or linked shunt 373.
Figure 31:
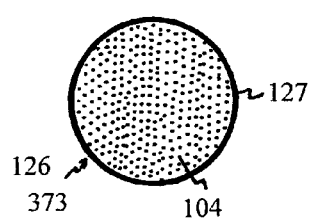
FIG. 31 shows cross-section of a disc shunt 126 or linked shunt 373, showing parallel oriented filaments 104 wrapped within a sheath or cover 127.
Figure 32:
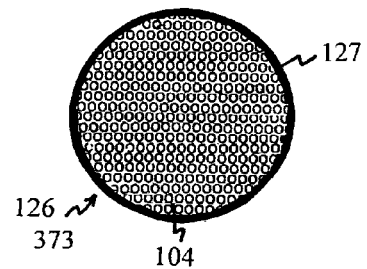
FIG. 32 cross-sections of a disc shunt 126 or linked shunt 373, showing parallel oriented tubular filaments 104 wrapped, encircled or enveloped by a sheath or cover 127.

A disc shunt 126 or linked shunt 373 is cut at a slanted angle, showing a cross-section of slanted or diagonally oriented shunt filaments 104, as shown in FIG. 30. FIG. 31 shows cross-sections of filaments 104 parallel to the disc shunt 126 or linked shunt 373, covered by a wrapper, sheath or cover 127. The parallel-oriented filaments 104 and wrapper 127 can be manufactured by extrusion. The filaments 104 can also be micro tubes, as shown in FIG. 32, parallel to the disc shunt 126 or linked shunt 373. A wrapper 127 is used to cover, retain, enclose or house the micro tubular filaments 104 to form the disc shunt 126 or linked shunt 373. Individual micro tubular filament 104 is capable of having capillary action, drawing nutrients/oxygen/pH buffer 131 through the disc shunt 126 or linked shunt 373 into the disc 100.

The filaments 104 are preferred to be made with biocompatible and hydrophilic material, absorbing, retaining or drawing fluid with nutrients/oxygen/pH buffer solutes 131 from a tissue with low osmolarity to the desiccated disc 100 with high osmolarity. The disc shunt 126 or linked shunt 373 can be a suture, approved for human implant. Instead of fastening tissue, the suture is used as a disc shunt 126 or linked shunt 373 to transport fluid from low to high osmolarity to alleviate back pain.

Figure 33:
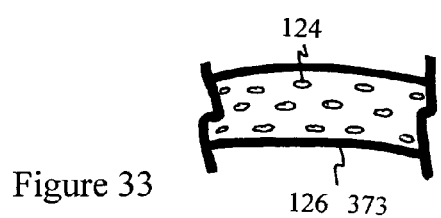
FIG. 33 shows a disc shunt 126 or linked shunt 373 made with sponge or foam with pores 124.
Figure 34:
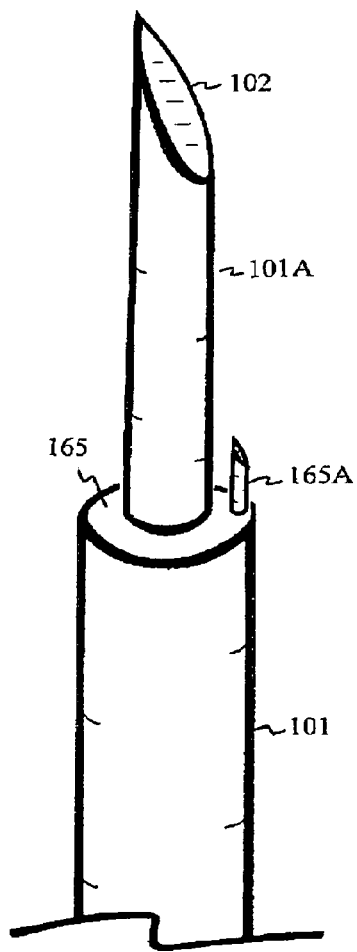
FIG. 34 shows a barb 165A protruding from the step 165 of the needle 101.
Figure 35:
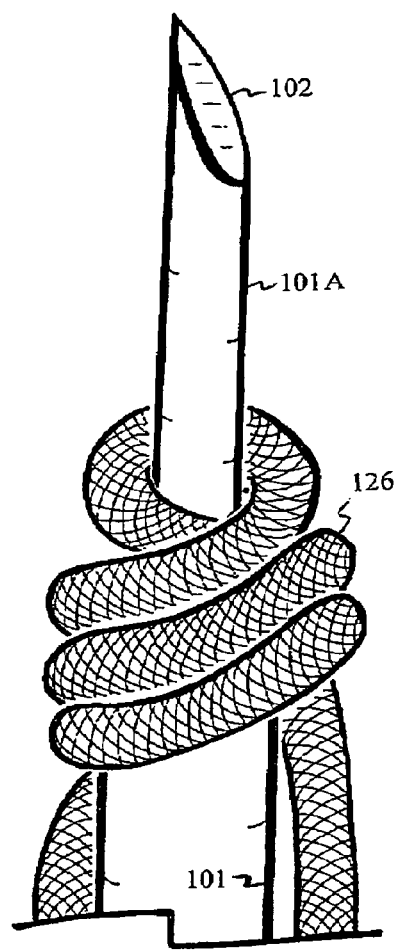
FIG. 35 shows spiraling of the disc shunt 126 over the shaft of the needle 101 by rotation of the needle 101.
Figure 36:
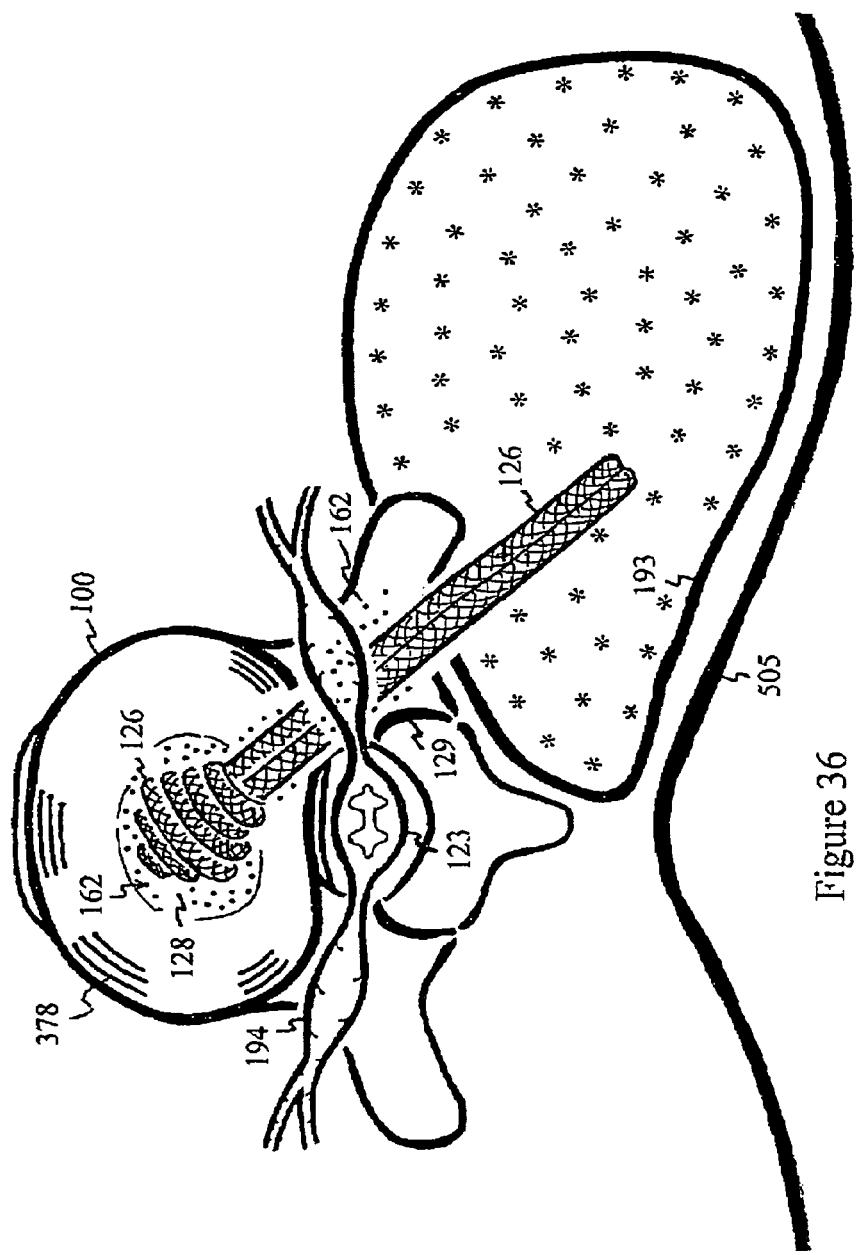
FIG. 36 shows the shunt spiral 126 as anchor to prevent migration of the disc shunt 126 from the intervertebral disc 101.

The disc shunt 126 or linked shunt 373 can be made with a hydrophilic sponge or foam with pores 124, as shown in FIG. 33, to transport and retain fluid in the disc 100. The pores 124 can be open, connecting to other pores 124. The pores 124 can also be closed, not connecting to other pores 124.

Disc cells isolated from advanced degenerated human discs 100 are still capable of producing collagen and glycosaminoglycans in tissue culture with abundant supply of nutrients in neutral pH. (Gruber H. E., Leslie K., Ingram J., Hoelscher G., Norton H. J., Hanley E. N. Jr.: Colony formation and matrix production by human anulus cells: modulation in three-dimensional culture, Spine, July 1, 29(13), E267-274, 2004. Johnstone B, Bayliss M T: The large proteoglycans of the human intervertebral disc, Changes in their biosynthesis and structure with age, topography, and pathology, Spine, March 15; 20(6):674-84, 1995.) Furthermore, stem cells have recently been found in degenerated discs. (Risbud M V, Gattapalli A, Tsai T T, Lee J Y, Danielson K G, Vaccaro A G, Albert T J, Garzit Z, Garzit D, Shapiro I M: Evidence for skeletal progenitor cells in the degenerate human intervertebral disc, Spine, November 1; 32(23), 2537-2544, 2007.) Nutrient 131 deficiency and acidic pH may hinder disc 100 repair in-vivo.

The disc shunt 126 or linked shunt 373 can be scaffolds for cell attachment, and spigots of nutrients/oxygen/pH buffering solute 131 for survival of disc cells. With a continual or renewable supply of nutrients/oxygen/pH buffer solutes 131, disc cells resume making biosynthetic products, such as the water-retaining glycosaminoglycans and collagen, the major components of the nucleus 128 and annulus 378. In sheep study, newly formed glycosaminoglycans can be seen in and around the disc shunt 126 and linked shunt 373 after 3 months, using Safranin histological staining.

The rate of sulfate incorporation for biosynthesizing glycosaminoglycans is pH sensitive. Chondroitin sulfate and keratan sulfate are two major water-retaining components in glycosaminoglycans. The maximum rate of sulfate uptake into the avascular disc 100 is within pH 7.2-6.9. The rate of sulfate uptake drops about 32-40% in acidic pH within the disc [Ohshima H, Urban J P: The effect of lactate and pH on proteoglycan and protein synthesis rates in the intervertebral disc. Spine, September: 17(9), 1079-82, 1992]. Hence, pH normalization or neutralization with sodium bicarbonate 131 through the disc shunt 126 or linked shunt 373 will likely increase production of the water-retaining glycosaminoglycans and swelling pressure of the shunted disc 100.

With a continual supply of nutrients 131, newly formed disc matrix increases osmolarity and enhances uptake of fluid into the shunted disc 100. Disc height is elevated or raised by the rehydrated disc 100, as depicted by arrows in FIG. 17. Additional uptake of fluid adds swelling pressure of the shunted disc 100, resulting in reduction of segmental or spinal instability. Muscle tension from guarding the spinal instability decreases. Load and pain of the facet joints 129 decrease. In essence, the disc shunts 126 or linked shunt 373 treats the etiology of disc degeneration and back pain, allowing the degenerated disc 100 to regenerate.

Furthermore, adenosine triphosphate, ATP, is the high-energy compound essential for driving biochemical reactions, including the biosynthesis of the water retaining glycosaminoglycans for sustaining compressive loads on the disc 100. Under anaerobic conditions, metabolism of each glucose molecule produces only two ATP and two lactic acids 162, which irritate adjacent nerves 118. When oxygen 131 permeates through the disc shunts 126 or linked shunt 373, thirty-six ATP can be produced from each glucose molecule through glycolysis, citric acid cycle and electron transport chain under aerobic conditions to energize disc regeneration and alleviate back pain.

In summary, the disc shunt 126 and linked shunts 373 transport nutrients/oxygen/pH buffer 131 to neutralize and reduce lactic acid 162, hydrate the desiccated nucleus 128 and nourish disc cells in the degenerated disc 100.

The disc shunt 126 and linked shunts 373 are hydrophilic with measurable characteristics under ambient temperature and pressure for transporting and retaining fluid to relieve pain and/or regenerate the degenerated disc 100. After saturation in water, the disc shunt 126 or linked shunts 373 gain weight between 10% and 500% by absorbing blood plasma 131. A healthy human disc 100 contains 80% water. The preferred water absorbency after water saturation is between 30% and 120%. The disc shunt 126 or linked shunt 373 can have pore sizes between 1 nano-meter and 200 micro-meters, serving as water retaining pockets or water transporting channels. Pores 124 of the disc shunt 126 or linked shunt 373 also function as scaffolding or housing for cell attachment and cellular proliferation. Water contact angle on the disc shunt 126 or linked shunt 373 is between 0 and 60 degrees. The preferred water contact angle of the disc shunt 126 or linked shunt 373 is between 0 and 30 degrees. Height of capillary action for drawing saline up the disc shunt 126 or linked shunt 373 is between 0.5 and 120 cm. The preferred height of capillary action of drawing saline is between 1 and 60 cm. Height of capillary action for drawing pork blood up the disc shunt 126 or linked shunt 373 is between 0.5 and 50 cm. The preferred height of capillary action for drawing pork blood up the disc shunt 126 or linked shunt 373 is between 1 cm and 25 cm. Saline siphoning transport rate through the disc shunt 126 and linked shunt 373 is between 0.1 and 10 cc per 8 hours in a humidity chamber. Human lumbar disc 100 loses between about 0.5 and 1.5 cc fluid per day due to compression. The saline siphoning transport rate through the disc shunt 126 or linked shunt 373 is preferred between 0.5 and 5 cc per 8 hours in a humidity chamber. Pork blood siphoning transport rate through the disc shunt 126 or linked shunt 373 is between 0.1 and 10 cc per 8 hours in a humidity chamber. The pork blood siphoning transport rate through the disc shunt 126 or linked shunt 373 is preferred between 0.5 and 3 cc per 8 hours in a humidity chamber.

The disc shunt 126 or linked shunt 373 used in the sheep and human clinical studies have the following physical properties under ambient temperature and pressure: (1) weight gain 80% after water saturation, (2) water contact angle zero degree, (3) height of capillary action 11 cm with pork blood, 40 cm with saline with blue dye, and (4) rate of siphoning pork blood 1.656+/−0.013 cc per 8 hours in a humidity chamber.

Approximately 85% back pain patients show no nerve impingement under MRI or CT. In a pilot clinical study, two patients without nerve impingement suffered chronic back pain with visual analog score 8-9 out of 10 (most severe). Seven days after implantation of the disc shunts 126 the visual analog score dropped to 2.5-3 for their back pain. Pain reduction continued for at least 1.5 years after implantation of the disc shunt 100. Acid neutralization is instantaneous. The quick and continual pain relief substantiate lactic acid 162 neutralization by the sodium bicarbonate 131 and patency of the disc shunt 126 to relieve acid burning of the adjacent sensory 118 and spinal 194 nerves.

The protruded step 165 of the stepped needle 101 in FIGS. 10, 10A and 13 can be made by machining or grinding. The protruded step 165 can also be created by a tube fitted as a sleeve over a solid needle 101A.

The stepped needle 101 can be made curved. The curved stepped needle 101 can be resiliently straightened within a rigid cannula. The rigid cannula can be made with a beveled distal end to facilitate insertion into the skin 505 and muscle 193 of the patient. Deployment of the cannula stops at the Kambin's Triangle 504. The stepped needle 101 is deployed from the rigid cannula, resuming the curved configuration into the nucleus 128 of the disc 100. The curved configuration of the needle 101 is particularly pertinent for shunt 128 deployment into L5-S1 lumbar disc 100, shielded by the iliac crests. The stepped needle 101 can be made with shape-memory material, such as nickel-titanium or spring-like stainless steel.

In United States, the average age of patients undergoing back surgery is 40-45 years old. The disc shunts 126 or linked shunt 373 is preferred to be made with permanent material to provide long-lasting pain relief. A wide range of non-degradable materials can be used to fabricate the shunts 126, 373. Polymers, such as Nylon, polytetrafluoroethylene, polypropylene, polyethylene, polyamide, polyester, polyurethane, silicon, poly-ether-ether-ketone, acetal resin, polysulfone, polycarbonate, silk, cotton, or linen are possible candidates. Fiberglass can also be a part of the shunts 126, 373 to provide capillarity for transporting nutrients 131 and waste.

Especially for investigative purposes, biodegradable shunts 126, 373 may provide evidence within weeks or months. Since the shunts 126, 373 degrade within months, any unforeseen adverse outcome would be dissipated. If the investigative-degradable shunts 126, 373 shows promise, permanent shunts 126, 373 can then be implanted to provide continuous benefits. The biodegradable shunt strands 126, 373 can be made with polylactate, polyglycolic, poly-lactide-co-glycolide, polycaprolactone, trimethylene carbonate, silk, catgut, collagen, poly-p-dioxanone or combinations of these materials. Other degradable polymers, such as polydioxanone, polyanhydride, trimethylene carbonate, poly-beta-hydroxybutyrate, polyhydroxyvalerate, poly-gama-ethyl-glutamate, poly-DTH-iminocarbonate, poly-bisphenol-A-iminocarbonate, poly-ortho-ester, polycyanoacrylate or polyphosphazene can also be used.

The shunts 126, 373, can be used as a drug delivery device for oral, intravenous or injectable medication into the nearly impenetrable disc 100 to treat infection, inflammation or pain. Drugs can be injected into the muscle 193 near the end portions 126B, 126C of the shunt 126 to be drawn into the shunted disc 100. Injection near the end portions of the shunt 126B, 126C is called peri-shunt injection.

Discitis is a painful infection or inflammatory lesion in the intervertebral disc 100 of adults and children (Wenger D R, Bobechko W P, Gilday D L: The spectrum of intervertebral disc-space infection in children, J. Bone Joint Surg. Am., 60:100-108, 1978. Shibayama M, Nagahara M, Kawase G, Fujiwara K, Kawaguchi Y, Mizutani J: New Needle Biopsy Technique for Lumbar Pyogenic Spondylodiscitis, Spine, 1 November, Vol. 35—Issue 23, E1347-E1349, 2010). Due to the avascular nature of the disc 100, oral or intravenous drugs cannot easily reach the bacteria or inflammation within the disc 100. Therefore, discitis is generally difficult to treat. However, the shunts 126, 373 can be used as a drug-delivery device. The shunts 126, 373 draw the systemic drugs from muscles 193 into the sealed, avascular disc 100.

*Staphylococcus aureus* is the most common bacteria found in discitis. The shunts 126, 373 can be loaded or coated with an antibiotic, such as nafcillin, cefazolin, dicloxacilin, clindamycin, bactrim, penicillin, mupirocin (bactroban), vancomycin, linezolid, rifampin, sulfamethoxazole-trimethoprim or other, to treat *staphylococcus aureus* infection. *Corynebacterium* is also found in discitis. The shunts 126, 373 can be loaded or coated with an antibiotic, such as erythromycin, vancomycin, eifampin, penicillin or tetracycline, to treat *corynebacterium* infection. Other antibiotics, such as cefdinir, metronidazole, tinidazole, cephamandole, latamoxef, cefoperazone, cefmenoxime, furazolidone or other, can also be used to coat the shunts 126, 373.

Inflammation in the disc 100 can cause excruciating pain. MRI can show inflammation at the endplates 105, and distinguish inflammatory classification as Modic I, II or III. The disc shunts 126, 373 can be coated or loaded with nonsteroidal anti-inflammatory drugs/analgesics (NSAID), such as aspirin, diflunisal, salsalate, ibuprofen, naproxen, fenoprofen, ketoprofen, flurbiprofen, oxaprozin, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, nimesulide, licofelone or other NSAID, to treat inflammation in the disc 100 for pain relief.

The disc shunts 126, 373 can also be coated or loaded with steroidal anti-inflammatory drugs/analgesics, such as betamethasone, budesonide, cortisone, dexamethasone, hydrocortisone, methylprednisolone, prednisolone, prednisone, triamcinolone or other steroid, to treat inflammation in the disc 100 for pain relief.

The shunts 126, 373 can be loaded or coated with anesthetics, such as procaine, amethocaine, cocaine, lidocaine, prilocaine, bupivacaine, levobupivacaine, ropivacaine, mepivacaine, dibucaine, methohexital, thiopental, diazepam, lorazepam, midazolam, etomidate, ketamine, propofol, alfentanil, fentanyl, remifentanil, sufentanil, buprenorphine, butorphanol, diamorphine, hydromorphone, levophanol, meperidine, methadone, morphine, nalbuphine, oxycodone, oxymorphone, pentazocine or other anesthetic, to provide instant pain relief.

The shunts 126, 373 can be loaded or coated with a muscle relaxant, such as succinylcholine, decamethonium, mivacurium, rapacuronium, atracurium, cisatracurium, rocuronium, vecuronium, alcuronium, doxacurium, gallamine, metocurine, pancuronium, pipecuronium, tubocurarine or other relaxant, to relief muscle tension and ache.

The shunts 126, 373 can be loaded or coated with buffering agents, such as sodium carbonate, sodium bicarbonate, potassium carbonate, potassium bicarbonate, magnesium carbonate, calcium carbonate, barium carbonate, potassium phosphate, sodium phosphate or other buffering agent, to neutralize lactic acid 162 and spontaneously alleviate pain caused by acid irritation or burn.

The shunts 126, 373 can be loaded or coated with alkaline agents, such as magnesium oxide, magnesium hydroxide, sodium hydroxide, potassium hydroxide, barium hydroxide, cesium hydroxide, strontium hydroxide, calcium hydroxide, lithium hydroxide, rubidium hydroxide, neutral amines or other alkaline agent, to neutralize lactic acid 162 and spontaneously alleviate pain caused by acid irritation.

The shunts 126, 373 can be loaded or coated with initial supplies of nutrients 131, such as sulfate, glucose, glucuronic acid, galactose, galactosamine, glucosamine, hydroxylysine, hydroxyproline, serine, threonine, chondroitin sulfate, keratan sulfate, hyaluronate, magnesium trisilicate, magnesium mesotrisilicate, magnesium oxide, magnosil, orthosilicic acid, magnesium trisilicate pentahydrate, sodium metasilicate, silanolates, silanol group, sialic acid, silicic acid, boron, boric acid, other mineral, other amino acid or nutrients 131, to enhance or initiate production of sulfated glycosaminoglycans and collagen within the degenerative disc 100.

Oral intake of antidepressants has shown temporary pain reduction or pain tolerance in back pain patients. Anti-depressants can be coated on the shunts 126, 373 to treat chronic back pain. The anti-depressant coating may include tricyclic antidepressant, serotonin-reuptake inhibitor, norepinephrine reuptake inhibitor, serotonin-norepinephrine reuptake inhibitor, noradrenergic/serotonergic antidepressants, norepinephrine-dopamine reuptake inhibitor, serotonin reuptake enhancers, norepinephrine-dopamine disinhibitors or monoamine oxidase inhibitor. The antidepressant can be amitriptyline, amitriptylinoxide, butriptyline, clomipramine, demexiptiline, desipramine, dibenzepin, dimetacrine, dosulepin/dothiepin, doxepin, duloxetine, imipramine, imipraminoxide, lofepramine, melitracen, metapramine, nitroxazepine, nortriptyline, noxiptiline, pipofezine, propizepine, protriptyline, quinupramine, amineptine, iprindole, opipramol, tianeptine, trimipramine, or other antidepressant.

Fibrous formation over the shunts 126, 373 may affect the exchange of nutrients 131 and waste between the disc 100 and bodily circulation or muscle 193. Immuno inhibitor can be coated or incorporated into the shunts 126, 373 to minimize fibrous formation or tissue response. Examples of immuno inhibitors include but are not limited to: actinomycin-D, aminopterin, azathioprine, chlorambucil, corticosteroids, crosslinked polyethylene glycol, cyclophosphamide, cyclosporin A, 6-mercaptopurine, methylprednisolone, methotrexate, niridazole, oxisuran, paclitaxel, polyethylene glycol, prednisolone, prednisone, procarbazine, prostaglandin, prostaglandin $E_1$, sirolimus, steroids or other immune suppressant drugs.

The shunts 126, 373 can be loaded or coated with a calcium channel blocker for inhibiting activation of neuro-receptor to alleviate pain. The calcium channel blocker can be dihydropyridines, phenylalkylamines, benzothiazepines, magnesium ion, Amlodipine, Felodipine, Isradipine, Lacidipine, Lercanidipine, Nicardipine, Nifedipine, Nimodipine, Nisoldipine, Verapamil, Diltiazem or other calcium channel blocker.

Healthy intervertebral discs 100 are avascular. To ensure avascular conditions, the shunts 126, 373 can be incorporated, coated or partially coated with an anti-angiogenic compound. Examples of anti-angiogenic compounds include, but are not limited to, Marimastat from British Biotech [a synthetic inhibitor of matrix metalloproteinases (MMPs)], Bay 12-9566 from Bayer (a synthetic inhibitor of tumor growth), AG3340 from Agouron (a synthetic MMP inhibitor), CGS 27023A from Novartis (a synthetic MMP inhibitor), COL-3 from Collagenex (a synthetic MMP inhibitor, Tetracycline® derivative), Neovastat from Aeterna, Sainte-Foy (a naturally occurring MMP inhibitor), BMS-275291 from Bristol-Myers Squib (a synthetic MMP inhibitor), TNP-470 from TAP Pharmaceuticals, (a synthetic analogue of fumagillin; inhibits endothelial cell growth), Thalidomide from Celgene (targets VEGF, bFGF), Squalamine from Magainin Pharmaceuticals (Extract from dogfish shark liver; inhibits sodium-hydrogen exchanger, NHE3), Combretastatin A-4 (CA4P) from Oxigene, (induction of apoptosis in proliferating endothelial cells), Endostatin collagen XVIII fragment from EntreMed (an inhibition of endothelial cells), Anti-VEGF Antibody from Genentech, [Monoclonal antibody to vascular endothelial growth factor (VEGF)], SU5416 from Sugen (blocks VEGF receptor signaling), SU6668 from Sugen (blocks VEGF, FGF, and EGF receptor signaling), PTK787/ZK 22584 from Novartis (blocks VEGF receptor signaling), Interferon-alpha (inhibition of bFGF and VEGF production), EMD121974 from Merck, KcgaA (small molecule blocker of integrin present on endothelial cell surface), CAI from NCI (inhibitor of calcium influx), Interleukin-12 from Genetics Institute (Up-regulation of interferon gamma and IP-10), IM862 from Cytran, Avastin, Celebrex, Erbitux, Herceptin, Iressa, Taxol, Velcade, TNP-470, CM101, Carboxyamidotriazole, anti-neoplastic urinary protein, Isotretionin, Tamoxifen, Tecogalan combrestatin, Squalamine, Cyclophosphamide, Angiostatin, Platelet factor-4, Anginex, Eponemycin, Epoxomicin, Epoxy-β-aminoketone, antiangiogenic antithrombin III, Canstatin, cartilage-derived inhibitor, CD59 complement fragment, Fibronectin fragment, Gro-beta, heparinases, heparin hexasaccharide fragment, human chorinonic gonadotropin, interferon (alpha, beta or gamma), interferon inducible protein (IP-10), Interleukin-12 (IL-12), Kringle 5 (plasminogen fragment), tissue inhibitors of metalloproteinases, 2-Methoxyestradiol (Panzem), placental ribonuclease inhibitor, plasminogen activator inhibitor, Prolactin 16 kD fragment, retinoids, Tetrahydrocortisol-S, Thrombospondin-1, transforming growth factor beta, Vasculostatin, and Vasostatin (calreticulin fragment).

The coating can be a lactic acid inhibitor or lactate dehydrogenase inhibitor, such as fluoropyruvic acid, fluoropyruvate, levulinic acid, levulinate, oxamic acid, oxamate, oxalic acid, oxalate, beta-bromopropionate, beta-chloropropionate, malonate, sodium formaldehyde bisufite, chloroacetic acid, alpha-chloropropionate, alpha-bromopropionate, acetoin, malic acid, acetaldehyde, acetylmercaptoacetic acid, thioglycolic acid, nicotinic acid, hydroxypyruvic, chloropyruvic, bromopyruvic, 2,3-dihydroxy-6-methyl-4-(1-methylethyl)-1-naphthoic acid, diethyl pyrocarbonate, 3-acetylpyridine adenine dinucleotide, 7-p-Trifluoromethylbenzyl-8-deoxyhemigossylic acid, dihydroxynaphthoic acids, N-substituted oxamic acids, gossypol, gossylic iminolactone, derivatives of gossypol, dihydroxynaphthoic acid, 2,3-dihydroxy-6-methyl-4-(1-methylethyl)-1-naphthoic acid, blue dye, reactive blue dye #2 or other.

The coating can be a chemotherapy drug to treat tumor in the spine.

In summary, the disc shunt 126 or linked shunt 373 alleviates back pain by (1) drawing sodium bicarbonate 131 from muscle 193 to neutralize lactic acid 162 and alleviate acid burn, (2) shunting fluid from muscle 193 to rehydrate the desiccated nucleus 128, (3) converting from anaerobic to aerobic conditions to reduce lactic acid 162 production, (4) increasing sulfate uptake in neutral pH for biosynthesis of glycosaminoglycans, (5) increasing ATP production from aerobic metabolism of sugars to drive biosynthetic reactions in disc 100, (6) increasing osmolarity to enhance fluid uptake, (7) building disc matrix to bulk up the disc 100 and take load off painful facet joints 129, and (8) delivering systemic drugs into avascular disc 100 to treat discitis or inflammation.

Unlike most surgical interventions of the spine, benefits of the disc shunts 126, 373 include (1) spinal motion preserving, (2) no tissue removal, (3) reversible by extraction, (4) microinvasive, (5) out-patient procedure, (6) approved implant material, (7) 15-minutes per disc procedure, (8) long-lasting and no-harm-done, (9) no incision, (10) compatible with drugs, conservative treatment or other surgical intervention, if needed, and (11) drug coated shunts 126, 373 if needed to expedite pain relief.

It is to be understood that the present invention is by no means limited to the particular constructions disclosed herein and/or shown in the drawings, but also includes any other modification, changes or equivalents within the scope of the claims. Many features have been listed with particular configurations, curvatures, options, and embodiments. Any one or more of the features described may be added to or combined with any of the other embodiments or other standard devices to create alternate combinations and embodiments.

Both ends 126B, 126C of the disc shunt 126 are located at the outside wall of a solid needle 101 for delivery and deployment of the disc shunt in the disc 100. The solid needle 101 can contain folk-like distal ends, with a slit between two sharp distal ends to house or drape the middle portion 126A of the disc shunt 126.

The solid needle 101 and shunt 126 can be used to (1) release ocular pressure to treat glaucoma, or (2) fasten torn meniscus and transport nutrients to expedite healing or reattachment of the partially vascular meniscus.

It should be clear to one skilled in the art that the current chemicals, biochemicals, drugs, methods, embodiments, materials, constructions, cells, tissues or sites are not the only uses for which the invention may be used. Different constructions, methods, materials or designs for the stepped needle 101, protruded step 165 or pull-line 460 can be substituted and used. The disc shunt 126 or linked shunt 373 can also be held by a pinching or clawing means, releasable by the operator. Different chemicals, minerals, drugs, cells or growth factors can also be used as part of intervention. The disc shunt 126 or linked shunt 373 can be called a conduit, wick, sponge, filament, braided filament, thread or absorbent. Nothing in the preceding description should be taken to limit the scope of the present invention.

What is claimed is:

1. A device for treatment of an intervertebral disc, the device comprising:
    a solid needle comprising a distal end, a protruded step and a proximal end, wherein said protruded step is located between said distal end and said proximal end,
    wherein said proximal end has an outside wall, and wherein said protruded step comprises at least one barb,
    a disc shunt comprising a first portion, a second portion and a middle portion, wherein said middle portion approximates said protruded step, and engages said at least one barb,
    wherein said distal end of said solid needle erects from said middle portion, and said first and second portions of said disc shunt approximate said outside wall,
    wherein said distal end, protruded step and said middle portion are sized and configured to enter an intervertebral disc,
    and wherein said first and second portions of said disc shunt are located outside the intervertebral disc, and are sized and configured to house within a muscle, thereby drawing blood from the muscle into the intervertebral disc to alleviate back pain.

2. The device of claim 1, wherein said protruded step comprises at least one indentation.

3. The device of claim 1, wherein said distal end is sharp.

4. The device of claim 1, wherein said solid needle is curved.

5. The device of claim 1, wherein said disc shunt connects to at least one linked shunt adapted to partially house in the intervertebral disc.

6. The device of claim 1, wherein said first portion connects to a pull line adapted to extend outside the skin.

7. The device of claim 1, wherein said second portion connects to a pull line adapted to extend outside the skin.

8. The device of claim 1, wherein said middle portion is thinner than said first or said second portions of said disc shunt.

9. The device of claim 1, wherein said disc shunt is made with braided filaments.

10. The device of claim 1, wherein said disc shunt is made with knitted filaments.

11. The device of claim 1, wherein said disc shunt is made with woven filaments.

12. The device of claim 1, wherein said disc shunt is made with filaments,
    and wherein at least some of said filaments are oriented length-wise parallel with said disc shunt.

13. The device of claim 1, wherein said disc shunt is made with micro-tubes.

14. The device of claim 13, wherein said micro-tubes are bundled by a wrapper.

15. The device of claim 1, wherein said disc shunt is made with sponge.

16. The device of claim 1, wherein said disc shunt has a water contact angle between 0 and 60 degrees.

17. The device of claim 1, wherein said disc shunt has pore sizes between 1 nano-meter and 200 micro-meters.

18. The device of claim 1, wherein said disc shunt has a drug coating.

19. A method for implanting a disc shunt to treat an intervertebral disc, the method comprising the steps of:
(a) puncturing skin and muscle into an intervertebral disc with a solid needle, wherein the solid needle comprises a distal end, a protruded step and a proximal end, wherein said protruded step is located between said distal end and said proximal end, and wherein said protruded step comprises at least one barb engaging a disc shunt,
(b) bridging said disc shunt between the muscle and the intervertebral disc, and
(c) withdrawing said solid needle from the skin, and leaving said disc shunt bridging between the muscle and the intervertebral disc, thereby transporting blood plasma from the muscle into the intervertebral disc through said disc shunt.

20. The method of claim 19, further comprising a step:
(d) twisting said solid needle.

21. The device of claim 1, wherein said middle portion includes a fortified ring, which is sized and configured to sit on the protruded step of the solid needle.

* * * * *